(12) United States Patent
Furry

(10) Patent No.: US 8,426,813 B2
(45) Date of Patent: *Apr. 23, 2013

(54) CHEMICAL LEAK INSPECTION SYSTEM

(75) Inventor: David W Furry, Blanket, TX (US)

(73) Assignee: Leak Surveys, Inc., Early, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,609

(22) Filed: May 2, 2012

(65) Prior Publication Data

US 2012/0273680 A1  Nov. 1, 2012

Related U.S. Application Data

(63) Continuation of application No. 11/298,862, filed on Dec. 10, 2005, now Pat. No. 8,193,496, which is a continuation of application No. PCT/US2004/012946, filed on Apr. 26, 2004.

(60) Provisional application No. 60/477,994, filed on Jun. 11, 2003, provisional application No. 60/482,070, filed on Jun. 23, 2003, provisional application No. 60/540,679, filed on Jan. 30, 2004.

(51) Int. Cl.
  *G01J 5/02* (2006.01)

(52) U.S. Cl.
  USPC ...................... 250/330; 250/339.03

(58) Field of Classification Search .................. 250/330, 250/339.03
  See application file for complete search history.

(56) References Cited

U.S. PATENT DOCUMENTS

| 3,032,655 | A | | 5/1962 | Romans et al. |
| 3,662,171 | A | | 5/1972 | Brengman et al. |
| 4,158,133 | A | * | 6/1979 | Spaeth et al. ............ 250/214 R |

(Continued)

FOREIGN PATENT DOCUMENTS

| EP | 0 536 586 B1 | 3/1995 |
| EP | 0 930 496 A2 | 7/1999 |

(Continued)

OTHER PUBLICATIONS

Hinnrichs, M., "Hand Held Imaging Spectrometer," Proceedings of the 31st Applied Imagery Pattern Recognition Workshop (Apr. 2002), IEEE Computer Society, USA.

(Continued)

*Primary Examiner* — David Porta
*Assistant Examiner* — Shun Lee
(74) *Attorney, Agent, or Firm* — Chamberlain Hrdlicka

(57) ABSTRACT

A method of visually detecting a leak of a chemical emanating from a component includes aiming a passive infrared camera system towards the component; filtering an infrared image with an optical bandpass filter, the infrared image being that of the leak; after the infrared image passes through the lens and optical bandpass filter, receiving the filtered infrared image with an infrared sensor device; electronically processing the filtered infrared image received by the infrared sensor device to provide a visible image representing the filtered infrared image; and visually identifying the leak based on the visible image. The passive infrared camera system includes: a lens; a refrigerated portion including the infrared sensor device and the optical bandpass filter (located along an optical path between the lens and the infrared sensor device). At least part of a pass band for the optical bandpass filter is within an absorption band for the chemical.

58 Claims, 31 Drawing Sheets

U.S. PATENT DOCUMENTS

| | | | |
|---|---|---|---|
| 4,390,785 | A | 6/1983 | Faulhaber et al. |
| 4,426,663 | A | 1/1984 | Evans et al. |
| 4,520,265 | A | 5/1985 | Griggs et al. |
| 4,543,481 | A | 9/1985 | Zwick |
| 4,555,627 | A | 11/1985 | McRae, Jr. et al. |
| 4,622,845 | A | 11/1986 | Ryan et al. |
| 4,712,195 | A | 12/1987 | Finger |
| 4,772,789 | A | 9/1988 | Maram et al. |
| 4,816,828 | A | 3/1989 | Feher |
| 4,841,149 | A | 6/1989 | Martin et al. |
| 4,904,996 | A | 2/1990 | Fernandes |
| 4,947,044 | A | 8/1990 | Pinson |
| 4,958,076 | A | 9/1990 | Bonne et al. |
| 4,963,742 | A | 10/1990 | Abernathy |
| 4,996,431 | A | 2/1991 | Bonne et al. |
| 4,999,614 | A | 3/1991 | Ueda et al. |
| 5,001,346 | A | 3/1991 | Barkhoudarian |
| 5,021,663 | A | 6/1991 | Hornbeck |
| 5,045,937 | A | 9/1991 | Myrick |
| 5,130,259 | A | 7/1992 | Bahraman |
| 5,166,789 | A | 11/1992 | Myrick |
| 5,197,295 | A | 3/1993 | Pundak |
| 5,202,682 | A | 4/1993 | Finger |
| 5,229,798 | A | 7/1993 | Brown |
| 5,241,380 | A | 8/1993 | Benson et al. |
| 5,300,976 | A | 4/1994 | Lim et al. |
| 5,306,913 | A | 4/1994 | Noack et al. |
| 5,430,293 | A | 7/1995 | Sato et al. |
| 5,479,258 | A | 12/1995 | Hinrichs et al. |
| 5,523,569 | A | 6/1996 | Hornfeld et al. |
| 5,550,373 | A | 8/1996 | Cole et al. |
| 5,550,375 | A | 8/1996 | Peters et al. |
| 5,650,624 | A | 7/1997 | Wong |
| 5,656,813 | A | 8/1997 | Moore et al. |
| 5,726,805 | A | 3/1998 | Kaushik et al. |
| 5,742,053 | A | 4/1998 | Rekunyk |
| 5,818,951 | A | 10/1998 | Schivley |
| 5,867,264 | A | 2/1999 | Hinrichs |
| 5,878,356 | A | 3/1999 | Garrot, Jr. et al. |
| 6,092,008 | A | 7/2000 | Bateman |
| 6,118,885 | A | 9/2000 | Wadsworth et al. |
| 6,157,486 | A | 12/2000 | Benson, Jr. et al. |
| 6,182,497 | B1 | 2/2001 | Krajci |
| 6,202,039 | B1 | 3/2001 | Finger |
| 6,243,483 | B1 | 6/2001 | Petrou et al. |
| 6,465,775 | B2 | 10/2002 | Mullins et al. |
| 6,580,450 | B1 | 6/2003 | Kersling et al. |
| 6,690,472 | B2 | 2/2004 | Kulp et al. |
| 6,766,226 | B2 | 7/2004 | Andersen |
| 6,853,452 | B1 | 2/2005 | Laufer |
| 8,193,496 | B2 * | 6/2012 | Furry .......................... 250/330 |
| 2003/0025081 | A1 | 2/2003 | Edner et al. |
| 2003/0075642 | A1 | 4/2003 | Silansky et al. |
| 2003/0086091 | A1 | 5/2003 | Hinnrichs et al. |
| 2003/0090670 | A1 | 5/2003 | Capetanopoulos et al. |
| 2003/0234862 | A1 | 12/2003 | Andersen |
| 2003/0236597 | A1 | 12/2003 | Andersen |
| 2004/0005085 | A1 | 1/2004 | Andersen |

FOREIGN PATENT DOCUMENTS

| | | | |
|---|---|---|---|
| JP | 52080888 | A | 7/1977 |
| JP | 01234759 | A | 9/1989 |
| JP | 05099778 | A | 4/1993 |
| JP | 2002365217 | A | 12/2002 |
| WO | 96/06345 | | 2/1996 |
| WO | 96/31766 | | 10/1996 |
| WO | 97/20167 | | 6/1997 |
| WO | 99/19712 | | 4/1999 |
| WO | 99/53350 | | 10/1999 |
| WO | 01/14873 | | 3/2001 |

OTHER PUBLICATIONS

Hinnrichs, M., et al., "Hyper-Spectral Imaging and Infrared Spectroscopy Using Pacific Advanced Technology's Image Multi-Spectral Sensor (IMSS) and Amber Engineering's Radiance 1 Camera," Critical Technology (Mar. 13, 1994) pp. 1-13, USA.

Hinnrichs, M., et al., "New Approach to Imaging Spectroscopy Using Diffractive Optics," Imaging Spectrometry III, Oct. 1997, pp. 194-205, Proceedings of SPIE vol. 3118, SPIE—The International Society for Optical Engineering, USA.

Kosterev, A.A., et al., "Methane Concentration and Isotopic Composition Measurements with a Mid-Infrared Quantum-Cascade Laser," Optic Letters, vol. 24, No. 23, (Dec. 1, 1999), 1762-1764, Optical Society of America, USA.

Radiance 1 Brochure; Nov. 14, 1992, Amber Engineering, Inc., USA.

PAT Industries, Inc., "IMSS: Another Promising Remote Air Quality Optical Sensing Technology," webpages from website of Gas Imaging Technology, LLC (a sub corporation of PAT Industries, Inc.), originally published Apr. 1, 2002 on the website of Pacific Advanced Technology (a sub corporation of PAT Industries, Inc.), <http://www.patinc.com/remote_air_quality_optical_senso.htm> and printed for re-submission on Oct. 19, 2006 from the website of Gas Imaging Technology, LLC, <http://www.gitinc.com/pressroom/pr-remote-sensing.htm>, PAT Industries, Inc., Santa.

PAT Industries, Inc., "Airborne Data Collection With IMSS Infrared Hyperspectral Sensor," webpages from website of Pacific Advanced Technology (a sub corporation of PAT Industries, Inc.), originally published in 2000 on the website of Pacific Advanced Technology <http://www.patinc.com/warlock.htm> and titled "Project WARLOCK" and printed for re-submission on Oct. 19, 2006 from the website of Pacific Advanced Technology <http://www.patinc.com/press_room/pr-airborne-sensor.htm>,PAT Industries, Inc., Santa Ynez, California, USA.

Radiance 1 Color Brochure (1993), Raytheon Corporation, USA.

Sandsten, J., et al., "Gas Imaging by Infrared Gas-Correlation Spectrometry," Optics Letters, Dec. 1, 1996, pp. 1945-1947, vol. 21, No. 23, Optical Society of America, USA.

Sandsten, J., et al., "Real-Time Gas-Correlation Imaging Employing Thermal Background," Optics Express, Feb. 14, 2000, pp. 92-103, vol. 6, No. 4, Optical Society of America, USA.

Merlin Brochure by Indigo Systems Corporation (2002), 6 pages.

U.S. Environment Protection Agency "Services Provider Directory" [online], [retrieved on Mar. 24, 2008]. Retrieved from the Internet<http://gitint.com/pressroom/pr-airborne-Sherlock.htm>.

Sherlock Brochure by Gas Imaging Technology (no dated), 3 pages.

"GIT and Coast Air Survey Successfully Test Sherlock for Airborne Pipeline Leak Monitoring" [online], [retrieved on Mar. 24, 2008]. Retrieved from the Internet<http://www.gitint.com/pressroonn/pr-airborne-Sherlock.htm>.

Fowler, et al. Evaluation of the SBRC 256×256 InSb focal plane array and preliminary specifications for the 1024×1024 InSb focal plane array, Proceddings of the SPIE vol. 1946 (1993), pp. 25-32.

Moyer, et al. Mid-wave infrared target source characteristics for focal plane applications, Proceedings of SPIE vol. 4719 (2002), pp. 63-74.

Tegstam, J., "High Sensitivity Infrared Camera Expedites Plant Leakage Detection," Offshore, Mar. 1, 2007, vol. 67, Issue 3, PennWell Corporation, Tulsa, Oklahoma.

"Measurement and Assessment of Equipment Leak Fugitives in Industrial Ethylene and Other Chemical Sources," Houston Advanced Research Center, Jun. 2003, pp. 1-5.

"Method 21: Determination of Volatile Organic Compound Leaks," Jul. 1, 2000, 40 CFR 60, Appendix A, pp. 1151-1166.

"Proposed Alternative Work Practice to Detect Leaks from Equipment," EPA, Apr. 6, 2006.

"GasFindIR Finds Even Small Fugitive Gas Emissions Quickly and Easily," Jan. 1, 2005, www.flirthermography.com/cameras/camera/1080, 2005, pp. 1-2, FLIR Systems, Inc.

Wimmers, J.T., et al., "Better, Smaller, IR IMagers Lead the Way to New Applications," Photonics Spectra, Dec. 1994, pp. 113-118.

"Analysis of Refinery Screening Data," American Petroleum Institute, AP Publication No. 310, Nov. 1997, pp. 1-62.

Gmachl, et al. "Methane Concentration and Isotopic Composition Measurements with a Mid-Infrared Quantum-Cascade Laser," Optic Letters, vol. 24, No. 23, (Dec. 1, 1999), pp. 1762-1764. Optical Society of America, USA.

Gas Measurement Instruments LTD, "Optical Methane Detector," PDF on Internet, (Oct. 10, 2000), <http://london.hetek.com/pdfs/gas/Optical%20Methane%20Detector.pdf>, Scotland.

Phan, Hue, "FTIR Analysis of Oxygenates for Motor Gasoline," AP-109, pp. 1-4, PDF on Internet from Midac Corporation (Apr. 20, 1998) <http://midac.com/apnotes/Ap-109pdf>, Costa Mesa, California, USA.

Wimmers, James T., et al. "Focal Plane Arrays: Better, Smaller IR Images for New Applications," The Photonics Design and Applications Handbook 1997, pp. H-212-H-217, USA.

Pacific Advanced Technology, "Recent Paper Presented at MSS Passive Sensors," Webpages from website of Pacific Advanced Technology, Mar. 2000, <http://www.patinc.com/Underground%20gas.%20leak.htm>, Charlestown, South Carolina, USA.

Pacific Advanced Technology, "IMSS Detects Methane Leak," Webpages from website of Pacific Advanced Technology, 2000, <http://www.patinc.com/Methane%20leak%20Detection.htm>, Santa Ynez, California, USA.

Pacific Advanced Technology, "Project WARLOCK," Webpages from website of Pacific Advanced Technology, 2000, ,http://www.patinc.com/warlock.htm>, Santa Ynez, California, USA.

Pacific Advanced Technology, "IMSS Image Mult-spectral Sensing," Webpages from website of Pacific Advanced Technology, 2000, <http://patinc.com/Imaging%20Spectrometer.htm>, Santa Ynez, California, USA.

Estrada, Andrea, "Seed Money," Webpages from website of Pacific Advanced Technology, (Oct. 29, 2000), <http://www.patinc.com/Seed%20Money.htm>, Santa Barbara, California, USA.

Spectrogon, "Bandbass Filters," Technical specification on Spectrogon website <http://www.spectrogon.com/bandpass.html>, USA.

Crisp, David, et al."All Molecules in Database," Table found on Internet at <http://vpl.ipac.caltech.edu/spectra/allmoleculeslist.htm>, CalTech, USA.

Boudon, V., et al. "Sulfur Hexaflouride (SF6)," Webpage found on Internet at <http://vpl.ipac.caltech.edu/spectra/sf6.htm>, CalTech, USA.

O'Brian, et al. "Methane (CH4)," Webpage found on Internet at <http://vpl.ipac.caltech.edu/spectra/ch4.htm>, CalTech, USA.

Tan, T.L., et al. "Ethylene (C2H4)," Webpage found on Internet at <http://vpl.ipac.caltech.edu/spectra/c2h4.htm>, CalTech, USA.

Fahr, A., et al. "Propylene (C3H6)," Webpage found on Internet at <http://vpl.ipac.caltech.edu/spectra/c3h6.htm>, CalTech, USA.

Metsala, et al.,"Butadiyne (C4H2) (diacetylene)," Webpage found on Internet at <http://vpl.ipac.caltech.edu/spectra/c4h2.htm>, CalTech, USA.

Tambe, Nikhil, "Applications of Stirling Cycle Refrigeration in Crycoolers," Seminar Paper (Nov. 16, 2004), found at <http://rclsgi.eng.ohio-state.edu/tambe/Geocities/Documents/Seminars/seminar.1.html, Ohio State University, USA.

Indigo Systems Corporation, "Merlin, The Ultimate Combination of Flexibility and Value in High-Performance Infrared Camera's," (Jan. 22, 2002), found PDF information on Italian distributor's website, Italy.

Indigo Systems Corporation, "Phoenix Product Description," (Sep. 11, 2000), found PDF information on Italian distributor's website, Italy.

Indigo Systems Corporation, "Merlin Mid, inSb MWIR Cmera, User's Guide," Version 120, 414-0001-10, (Dec. 3, 2002), Santa Barbara, USA.

* cited by examiner

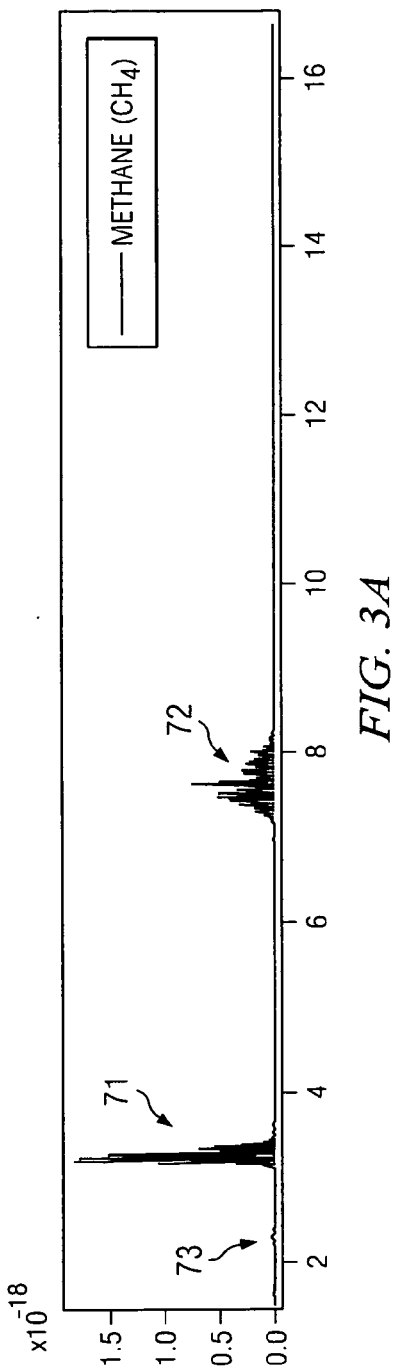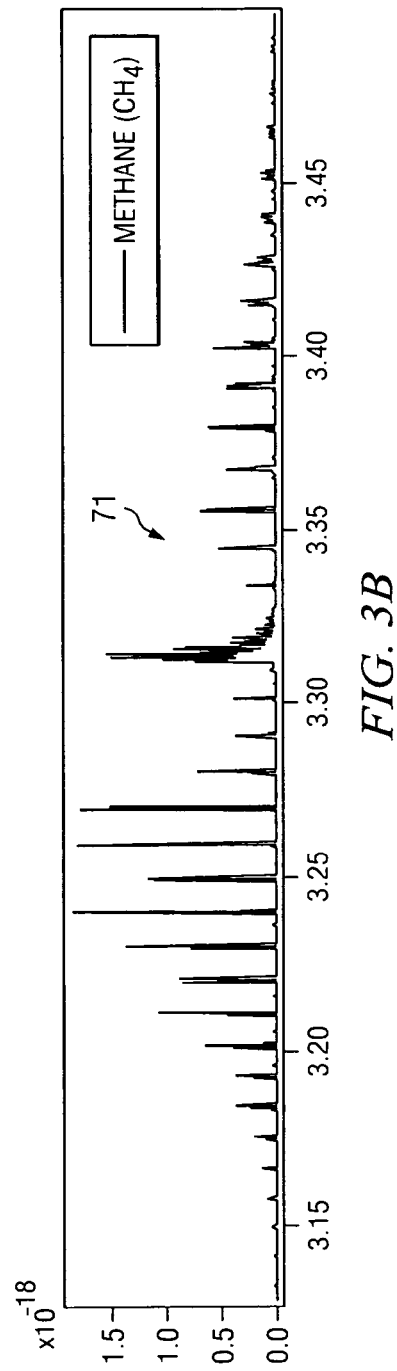
FIG. 3A
FIG. 3B

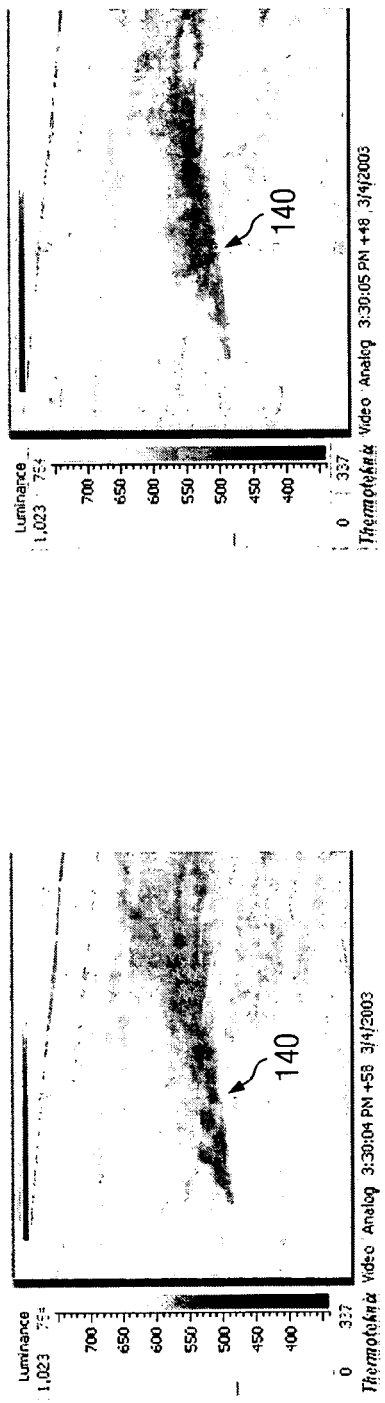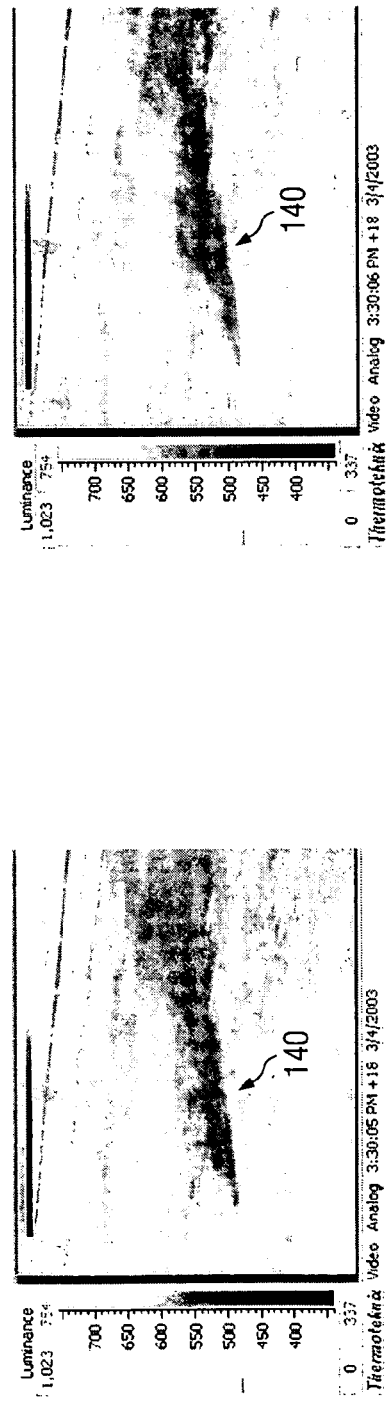
FIG. 23B
FIG. 23D
FIG. 23A
FIG. 23C

CHEMICAL LEAK INSPECTION SYSTEM

CROSS REFERENCE TO RELATED APPLICATIONS

This application is a continuation of U.S. patent application Ser. No. 11/298,862, filed Dec. 10, 2005, entitled "Methods for Performing Inspections and Detecting Chemical Leaks Using an Infrared Camera System," which is a continuation of PCT International Application No. PCT/2004/012946, filed Apr. 26, 2004, entitled "Systems and Methods for Performing Inspections and Detecting Chemical Leaks Using an Infrared Camera System," which claims the benefit of U.S. Provisional Patent Application No. 60/477,994, filed Jun. 11, 2003, entitled "Method of Detecting Gas Leaks Using and Infrared Camera System," U.S. Provisional Patent Application No. 60/482,070, filed Jun. 23, 2003, entitled "Method of Detecting Gas Leaks Using and Infrared Camera System," and U.S. Provisional Patent Application No. 60/540,679, filed Jan. 30, 2004, entitled "Method of Detecting Gas Leaks Using an Infrared Camera System," all of which are incorporated herein by reference in their entirety for all purposes.

TECHNICAL FIELD

The present invention relates generally to visually detecting and identifying chemical, gas, and petroleum product leaks using an infrared (IR) camera system.

BACKGROUND

In the oil and gas business, in the petro-chemical industry, in processing plants, and for utility companies and utility providers, for example, often more time and money is spent trying to find leaks than fixing leaks. One of the biggest challenges is trying to find the leaks using conventional methods. Many conventional methods can simply miss a leak and not detect it if the detector is not properly positioned over or downwind of the leak. Also, many conventional methods are very time consuming and labor intensive, which leads to more expense. Hence, there is a great need for a faster, more accurate, and less expensive method of detecting such leaks.

Petroleum products, such as liquid, gas, and liquid/gas forms of hydrocarbon compounds (e.g., fossil fuels), are often transmitted or channeled in pipes. The conventional method of surveying lines for petroleum product leaks or for detecting petroleum product leaks in general is with a FLAME-PACK ionizer detector (also sometimes referred to as a "sniffer" device). Another recently developed system uses an active infrared system (having a transmitting infrared source and a receiving sensor) for detecting petroleum product fumes. However, such systems require that the detector be within the stream or plume of the petroleum product leak. These tests merely detect the presence of petroleum product fumes at or upwind of the detector. They do not provide a visual image of the leak. Also, these prior testing methods require the detector to be in the immediate proximity of the leak, which may be dangerous and/or difficult for the inspector.

Prior infrared systems designed for evaluating rocket fumes, for example, would provide an unfocused and fuzzy image, in which it was difficult to make out background objects. For example, using an infrared camera that images a broad range of infrared wavelengths (e.g., 3-5 microns) typically will not be useful in detecting small leaks. One system uses a variable filter that scans through different bandwidths in an attempt to identify the bandwidth of the strongest intensity (as quantified by the system). The purpose of this system was an attempt to identify the chemical make-up of a rocket exhaust based on the wavelength at which the intensity was greatest for the rocket plume. However, this system is not designed to provide a focused visual image to view the rocket exhaust.

Others have attempted to visualize petroleum product leaks using infrared cameras using a "warm" filter setup and/or an active infrared camera system. A warm filter setup is one in which a filter is used to limit the wavelengths of light that reach the infrared sensor, but the filter is not in a cooled or refrigerated portion of the camera, if the camera even has a refrigerated portion. Such systems have not been able to provide a focused image capable of quickly and easily detecting small leaks, nor being capable of detecting leaks from a distance (e.g., from a helicopter passing over a line). Other systems are active and require a laser beam to be projected through the area under inspection in order to detect the presence of a chemical emanating from a component. However, with such systems, typically the narrow laser beam must cross the flow stream for the leak to be detected. Hence, a leak may be missed if the laser beam does not cross the path of the leak and such systems often are unable to reliably find small leaks. Hence, a need exists for a way to perform a visual inspection to find leaks with reliability and accuracy, while being faster and more cost effective than existing leak survey methods.

The U.S. Environmental Protection Agency (EPA) has proposed rules to allow visual inspections using infrared cameras in performing leak inspection surveys. However, due to the lack of detection abilities and poor performance demonstrated by other prior and current systems, the EPA had not yet implemented such rules. Thus, even the EPA has been waiting for someone to provide a system or way of reliably and accurately detecting leaks of various sizes.

SUMMARY OF THE INVENTION

The problems and needs outlined above may be addressed by embodiments of the present invention. In accordance with one aspect of the present invention, a passive infrared camera system adapted to provide a visual image of a chemical emanating from a component having the chemical therein, is provided. The passive infrared camera system includes a lens, a refrigerated portion, and a refrigeration system. The refrigerated portion has therein an infrared sensor device and an optical bandpass filter. The infrared sensor device is adapted to capture an infrared image from the lens. The optical bandpass filter is located along an optical path between the lens and the infrared sensor device. At least part of a pass band for the optical bandpass filter is within an absorption band for the chemical. The refrigeration system is adapted to cool the refrigerated portion of the infrared camera system.

In accordance with another aspect of the present invention, a method of visually detecting a leak of a chemical emanating from a component, is provided. This method includes the following steps described in this paragraph. The order of the steps may vary, may be sequential, may overlap, may be in parallel, and combinations thereof. A passive infrared camera system is aimed towards the component. The passive infrared camera system includes a lens, a refrigerated portion, and a refrigeration system. The refrigerated portion includes therein an infrared sensor device and an optical bandpass filter. The optical bandpass filter is located along an optical path between the lens and the infrared sensor device. At least part of a pass band for the optical bandpass filter is within an absorption band for the chemical. The refrigeration system is adapted to cool the refrigerated portion. An infrared image is filtered with the optical bandpass filter. The infrared image is that of the leak of the chemical emanating from the component. After the infrared image passes through the lens and optical bandpass filter, the filtered infrared image of the leak is received with the infrared sensor device. The filtered infrared image received by the infrared sensor device is electronically processed to provide a visible image representing the filtered infrared image. The leak is visually identified based on the visible image representing the filtered infrared image provided by the infrared camera system.

The foregoing has outlined rather broadly features of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The following is a brief description of the drawings, which illustrate exemplary embodiments of the present invention and in which:

FIGS. 3A-3D are absorption graphs for methane;

FIGS. 23A-31B are example images obtained using an embodiment of the present invention;

DETAILED DESCRIPTION OF THE ILLUSTRATIVE EMBODIMENTS

Figure 1:
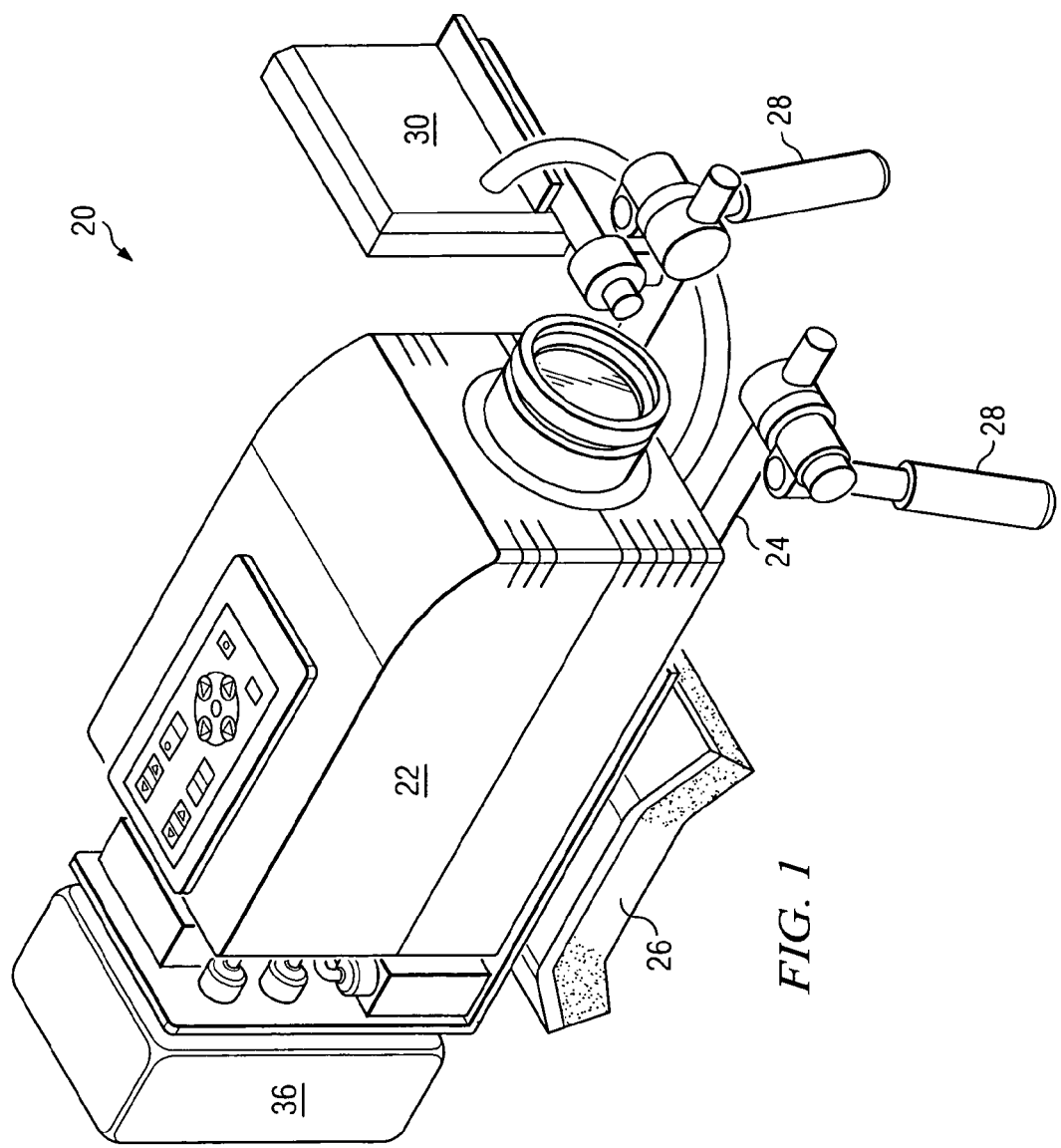
FIG. 1 is perspective view of a chemical leak detection system of a first embodiment.

Referring now to the drawings, wherein like reference numbers are used herein to designate like or similar elements throughout the various views, illustrative embodiments of the present invention are shown and described. The figures are not necessarily drawn to scale, and in some instances the drawings have been exaggerated and/or simplified in places for illustrative purposes only. One of ordinary skill in the art will appreciate the many possible applications and variations of the present invention based on the following illustrative embodiments of the present invention.

FIG. 1 shows a chemical leak inspection system 20 in accordance with a first embodiment of the present invention. The chemical leak inspection system 20 of the first embodiment includes a passive infrared camera system 22. The passive infrared camera system 22 of the first embodiment is adapted to provide a visible image representing a filtered infrared image of a chemical emanating (e.g., leaking) from a component having the chemical therein, as discussed in more detail below.

As shown in FIG. 1, the infrared camera system 22 may be mounted on a frame 24. A shoulder-rest portion 26 and handles 28 may be attached to the frame 24, as shown in FIG. 1. The shoulder-rest portion 26 and the handles 28 aid in holding the system 20 during an inspection (see e.g., FIG. 21 discussed below). Typically during an inspection using this system 20, an inspector will walk around various components while carrying the system 20 on his shoulder and aiming the system 20 toward the components to look for leaks. In other embodiments, however, the camera system 22 may be handled or carried in other ways (e.g., by hand, from a vehicle, on a vehicle, on a tripod, on a gyro-stabilized platform, by a harness, etc.). Also, as discussed further below, inspections using an embodiment of the present invention may be performed from a vehicle (moving and not moving).

Figure 21:
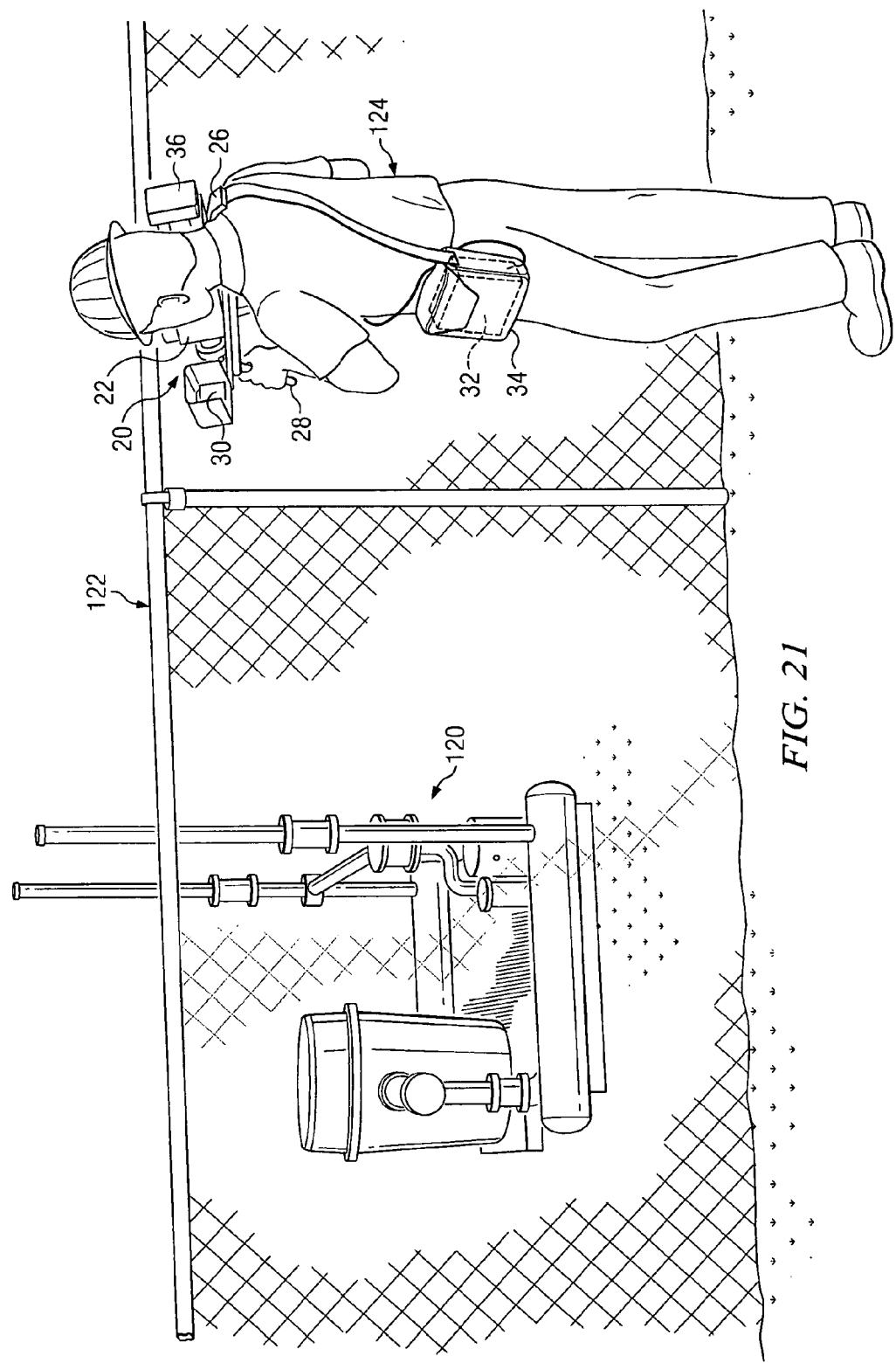
FIG. 21 shows an inspector using an embodiment of the present invention.
Figure 24A:
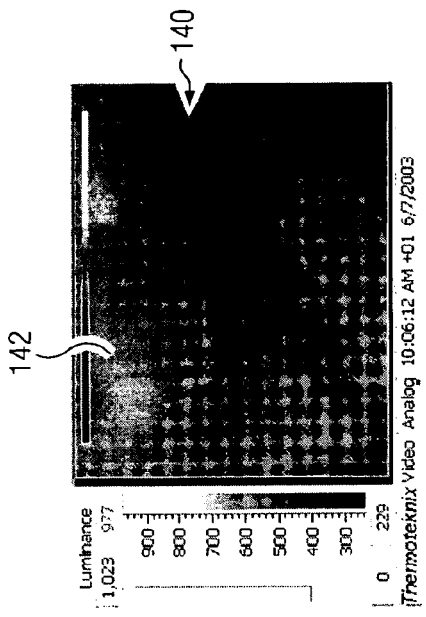
Figure 24B:
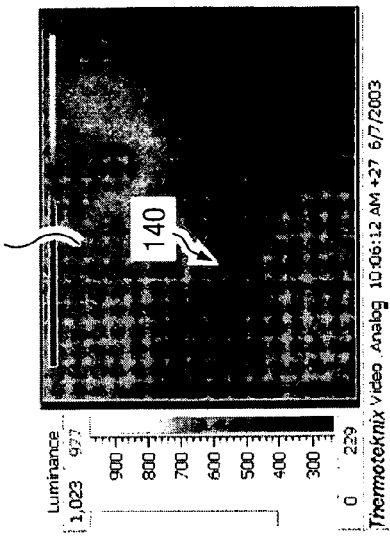
Figure 24C:
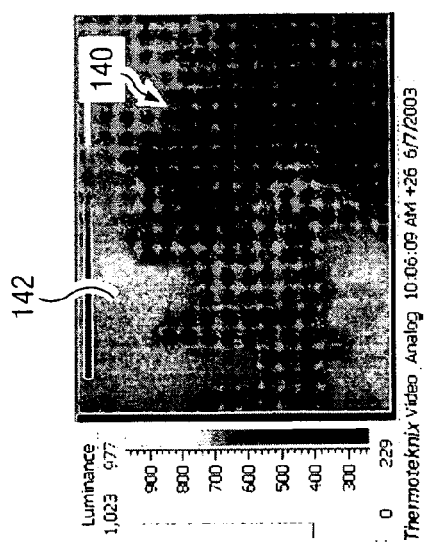
Figure 24D:
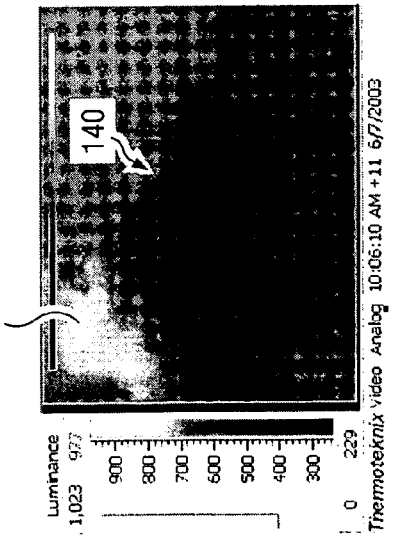
Figure 25A:
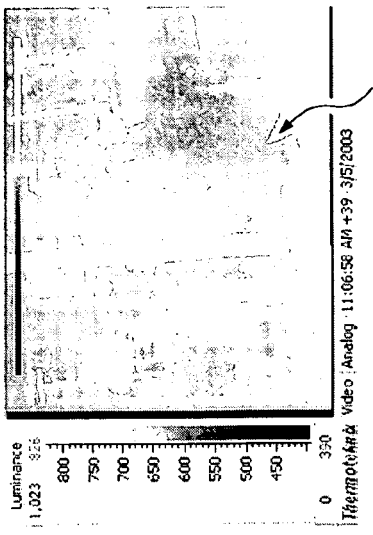
Figure 25B:
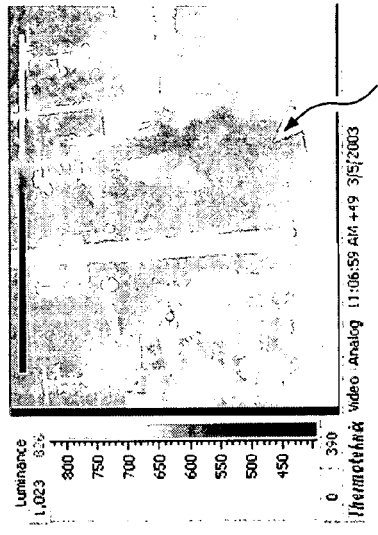
Figure 25C:
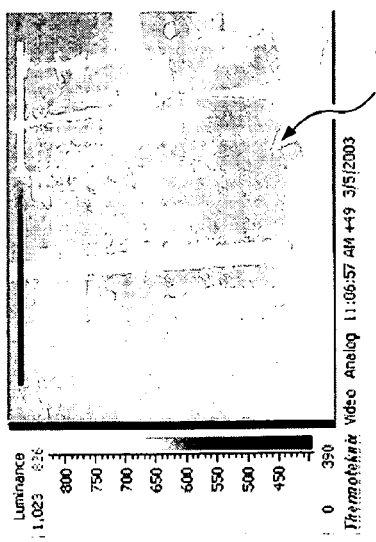
Figure 25D:
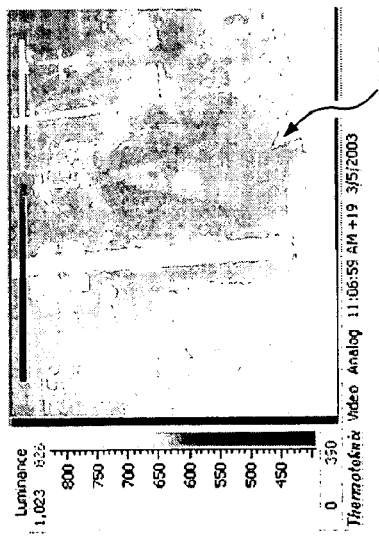

The leak inspection system 20 of the first embodiment also has a flat-panel display screen 30 (e.g., LCD display) electrically coupled to the infrared camera system 22 (see e.g., FIG. 1). The visible images (representing the filtered infrared images) provided by the camera system 22 may be displayed on the display screen 30 during an inspection. The system 20 preferably includes a video recording device 32 (not shown in FIG. 1, but see, e.g., FIG. 21 discussed below) electrically coupled to the camera system 22 for recording images obtained by the camera system 22 during use of the system 20. The video recording device 32 may be attached to the frame 24 or it may be carried separately by the inspector (e.g., in a backpack or in a carrying case 34 as shown in FIG. 21), for example. The video recording device 32 may record the images in a digital and/or analog format, for example. Thus, during use of the system 20 for locating a leak, an inspector may find a leak visually, as viewed on the display screen 30, and then record detailed and focused images of the leak using the video recording device 32 for future observation and/or for obtaining a record of the leak.

The system 20 of the first embodiment has a battery 36 electrically coupled to the infrared camera system 22. Preferably, the system 20 is powered by the battery 36 during use of the system 20 to allow the inspector to move about freely during an inspection. In other embodiments, however, the system 20 may be powered via a power cord by electricity from a wall outlet, from a generator, or from an alternator of a vehicle, for example. Typically, it will be less preferable to power the system 20 via a power cord, as it may limit the mobility of the inspector and/or slow down the inspection process.

Figure 2:
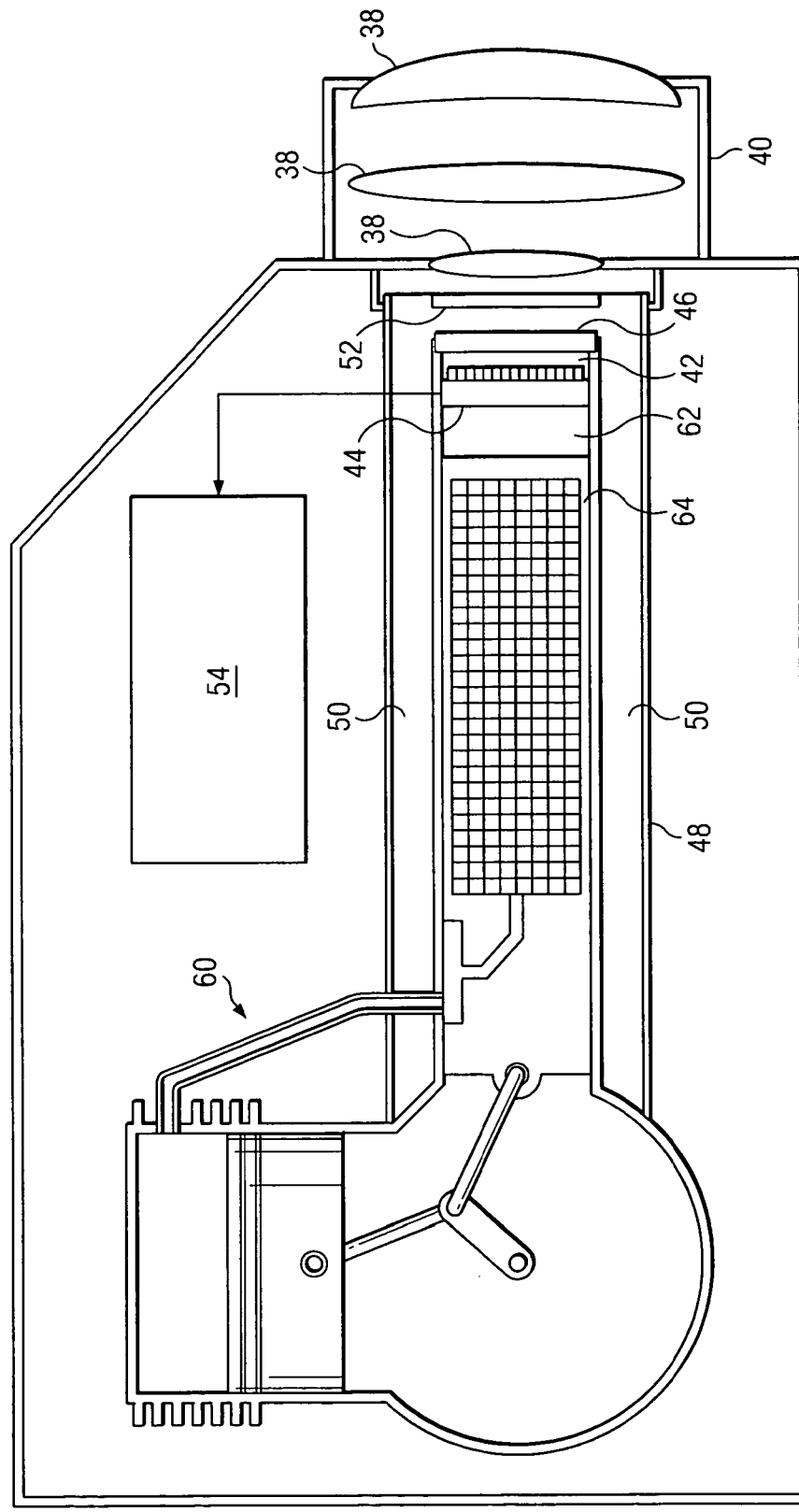
FIG. 2 is a schematic of the infrared camera system of the chemical leak detection system of FIG. 1.

FIG. 2 is a schematic of the infrared camera system 22 of FIG. 1 to illustrate some of the components therein. In the first embodiment, the passive infrared camera system 22 has one or more lenses 38 in a lens assembly 40 for optically focusing the image. Preferably, the lens assembly 40 is removable to allow for different lens assemblies (e.g., with different focal ranges) to be removably installed on the camera system 22. The camera system 22 has a refrigerated portion 42 that comprises therein an infrared sensor device 44 and an optical bandpass filter 46. The refrigerated portion 42 is preferably defined by an interior of a Dewar container 48. Preferably, the Dewar container 48 has an evacuated region 50 surrounding the refrigerated portion 42 to provide insulation. The Dewar container 48 may be made from metal and it has at least one Dewar window 52 for allowing the infrared image from the lens assembly 40 to enter into the refrigerated portion 42. The infrared sensor device 44, located in the refrigerated portion 42, is adapted to capture infrared images that come into the refrigerated portion 42 via the lens assembly 40. In a preferred embodiment, the infrared sensor device 44 is a focal plane array (FPA) of Indium Antimonide (InSb) sensors (e.g., a 320×256 matrix) to provide a high sensitivity in the 3-5 micron range of infrared light, for example. Other materials may be used for the infrared sensor device 44 in other embodiments to provide high sensitivity to other wavelength ranges of infrared light. The infrared sensor device 44 is electrically coupled to other electronic components (represented generally by block 54 in FIG. 2), which may be inside and/or outside of the camera system 22. The design of the infrared sensor device 44 and the electronic components 54 for the camera system 22 may vary for other embodiments of the present invention.

The refrigerated portion 42 is cooled by a refrigeration system 60. The refrigeration system 60 used may vary for different embodiments of the present invention. Preferably, the refrigeration system 60 is capable of maintaining the temperature in the refrigerated portion 42 below about 100 K (i.e., less than about −173° C.). More preferably, the temperature in the refrigerated portion 42 is maintained between about 75 K and about 85 K by the refrigeration system 60. In the first embodiment, the refrigeration system 60 includes a closed-cycle Stirling cryocooler, as illustrated schematically in FIG. 2. The actual configuration of the Stirling cycle cryocooler 60 for a given embodiment may vary from that shown in FIG. 2. A cold finger 62 may be used to provide a thermal communication between the refrigerated portion 42 and a regenerator cylinder 64, as shown in FIG. 2. The Stirling cycle cryocooler 60 may use helium as a refrigerant or cryogenic fluid, for example. In a preferred embodiment, a closed-cycle Stirling cryocooler 60 may be used to thermally stabilize the temperature in the refrigerated portion 42 at about 77 K, for example. A preferred infrared camera system 22, for example, for use in an embodiment of the present invention is a Merlin™ mid-wavelength infrared (MWIR) high-performance camera available from Indigo Systems, Inc. in California.

As illustrated schematically in FIG. 2, the optical bandpass filter 46 is located along an optical path between the lens assembly 40 and the infrared sensor device 44, and hence infrared images are filtered by the optical bandpass filter 46 before reaching the infrared sensor device 44. The optical bandpass filter 46 of the first embodiment has a pass band (bandpass transmittance range) located between about 3100 nm and about 3600 nm. Because the optical bandpass filter 46 is cooled, i.e., located in the refrigerated portion 42, in the first embodiment, the filter 46 works better than if it were not cooled (e.g., not in the refrigerated portion 42), and it allows for a more focused image than if a warm (uncooled) optical bandpass filter configuration were used. In a preferred embodiment, the optical bandpass filter 46 is cooled to a temperature below about 100 K. Cooling the optical bandpass filter 46 in the refrigerated portion 42 (i.e., "cold" filter configuration) provides a greater temperature contrast (greater temperature differential) between the leaking chemical and the optical bandpass filter 46, which increases the sensitivity of the camera system 22 for imaging the leaking chemical. Cooling the optical bandpass filter 46 effectively reduces the background noise of the filter 46 (as perceived by the infrared sensor device 44). When the optical bandpass filter 46 is not cooled (i.e., "warm" filter configuration), the level of background noise produced by the filter itself is much higher (relative to a cold filter configuration) and thus the sensitivity to detecting the infrared light absorbed by the leaking chemical after the infrared image passes through the warm filter is reduced. Also, in a warm filter configuration, the temperature difference between the optical bandpass filter and the leaking chemical is much smaller than that of a "cold" filter.

The camera system 22 of FIGS. 1 and 2, of the first embodiment, is a passive infrared camera system. Hence, the camera system 22 relies on the background (whatever the background may be) to be a reflector of environmental light and heat to the camera system 22. Most chemicals of interest have one or more absorbance bands (wavelength ranges where the absorbance of infrared light is orders of magnitude higher). For example, FIGS. 3A-3D show absorbance graphs for methane (CH4) gas based on experimental data.

In each graph of FIGS. 3A-3D, the vertical axis is absorbance (unitless) and the horizontal axis is wavelength (μm) of infrared light. Transmission and absorbance are inversely related. Transmission is typically defined as the fraction of light that reaches a detector after passing through a sample (e.g., an optical filter, a gas):

$$T = I/Io \text{ or } \% T = 100(I/Io),$$

where I denotes light intensity reaching the detector after passing through a sample, Io denotes light intensity of a reference beam or source beam with no sample present, T denotes transmission (expressed as a fraction), and % T denotes transmission (expressed as a percentage). Absorbance is a logarithmic scale that increases as transmission decreases:

$$A = \log 10 \, (Io/I),$$

where A denotes absorbance. Infrared radiation is often measured in units of wavelength (e.g., microns or nanometers). Also, infrared radiation is sometimes measured in units called wavenumbers ($cm^{-1}$):

$$\text{wavenumber } (cm^{-1}) = 107/\lambda = E/hc \times 1/100,$$

where $\lambda$ is wavelength in nanometers, E is energy (J), h is Planck's constant ($6.626 \times 10^{-34}$ J·s), and c is the speed of light ($3.0 \times 10^8$ m/s). Hence, the wavenumber of a light wave is directly proportional to its wavelength and its energy.

Figure 3C:
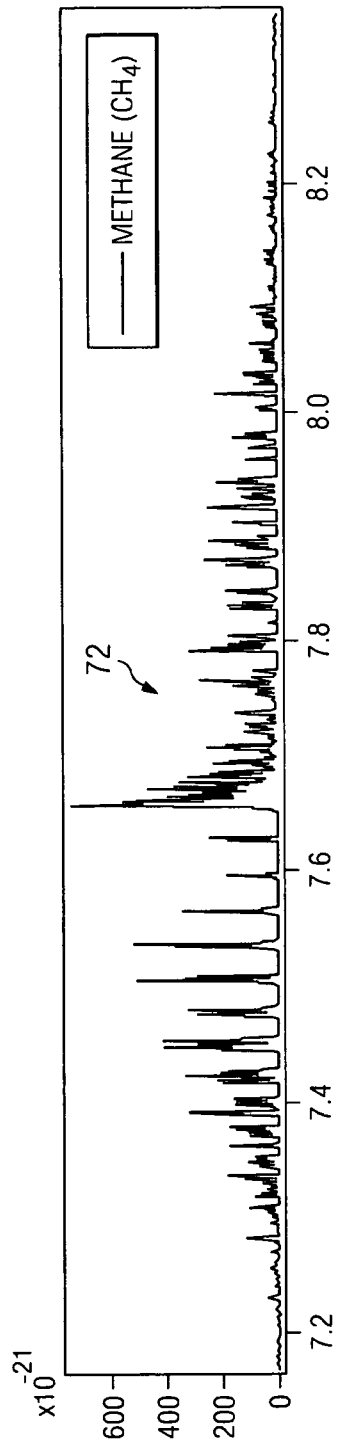
Figure 3D:
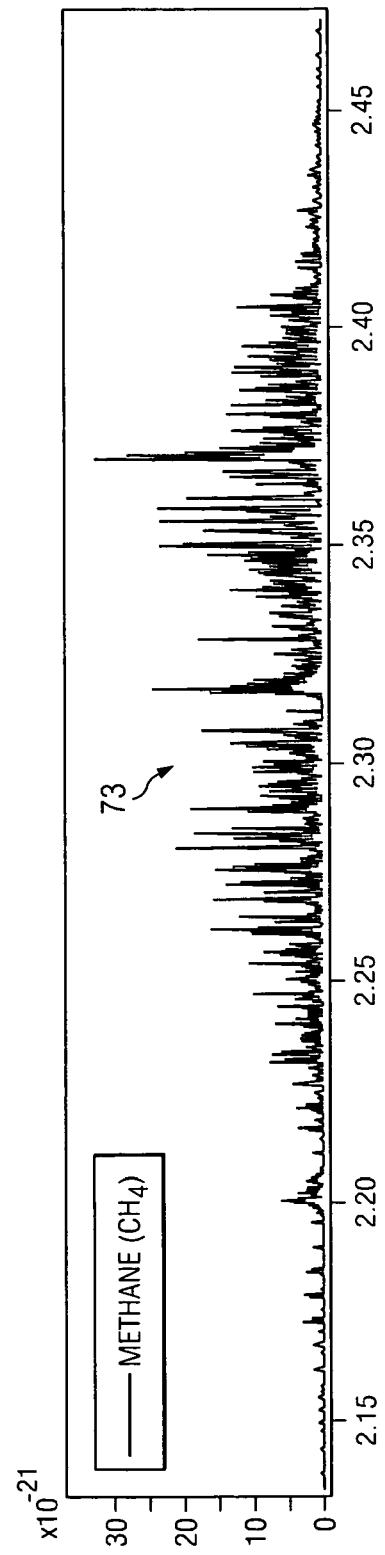

FIG. 3A shows the absorbance of methane from about 1.5 µm to about 16.5 µm (infrared light). Note that for methane, there are two major absorbance bands 71, 72 where the absorbance of infrared light is much higher (orders of magnitude higher) than at other adjacent wavelengths. A first absorbance band 71 is located between about 3.1 µm and about 3.6 µm, and a second absorbance band 72 is located between about 7.2 µm and about 8.2 µm (see FIG. 3A). FIG. 3B shows a range of wavelengths between about 3.15 µm and about 3.45 µm to illustrate the first absorbance band 71 of FIG. 3A in more detail. Note that the vertical scale for the graph in FIG. 3A is the same as that of FIG. 3B. FIG. 3C shows a range of wavelengths between about 7.2 µm and about 8.2 µm to illustrate the second absorbance band 72 of FIG. 3A in more detail. Note that the vertical scale of the graph in FIG. 3C is orders of magnitude smaller than that of FIG. 3A. There are also 1 other absorbance bands (73) for methane in the range shown in FIG. 3A, but they have orders of magnitude less absorbance than the first and second absorbance bands 71, 72. For example, a third absorbance band 73 is shown in FIG. 3A at about 2.3 µm. FIG. 3D shows a range of wavelengths between about 2.15 µm and about 2.45 µm to illustrate the third absorbance band 73 in more detail. The vertical scale for the graph in FIG. 3D is orders of magnitude smaller than that of FIGS. 3A-3C. Hence, methane has a much higher absorbance of infrared light between about 3.1 µm and about 3.5 µm (overlapping or within the first absorption band 71). Thus, an infrared camera system 22 adapted to detect infrared light between about 3-5 µm, for example, will have high sensitivity for imaging methane between about 3.1 µm and about 3.5 µm. The absorbance of methane at the second absorbance band 72 (see FIG. 3A) may be easily detected as well by an infrared camera system 22 adapted to detect infrared light at that range (e.g., about 7-8 µm).

In a preferred embodiment of the present invention adapted to visually detect a certain chemical (and perhaps other chemicals as well) leaking from a component, the optical bandpass filter 46 is located in the refrigerated portion 42 of the infrared camera system 22 and the optical bandpass filter 46 has a pass band that is at least partially located in an absorption band for the chemical. For example, in the first embodiment, the optical bandpass filter 46 has a pass band 80 located between 3200 nm and 3550, as illustrated by the transmission curve for the filter 46 in FIG. 4. The first embodiment is adapted to visually detect methane, for example, (as well as other chemicals). As discussed above, methane has a first absorption band 71 (see FIGS. 3A and 3B) located between about 3100 nm and about 3500 nm.

Figure 4:
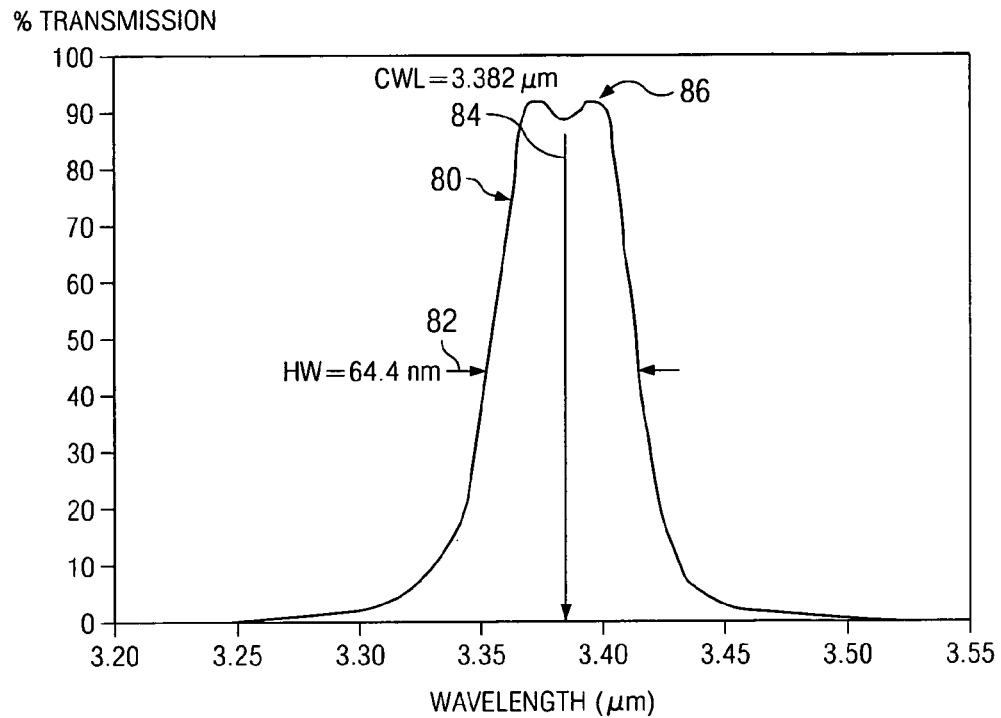
FIG. 4 is a transmission curve illustrating a pass band of an optical bandpass filter.

The optical bandpass filter 46 of the first embodiment has a full width at half maximum (HW) 82 of about 64.4 nm, a center wavelength 84 of about 3382 nm, and a peak transmission 86 of about 91.16%, as shown in transmission curve of FIG. 4. The optical bandpass filter 46 of the first embodiment is a single bandpass passive filter formed on a quartz ($SiO_2$) substrate, which is currently preferred. A preferred bandpass filter providing such performance characteristics may be obtained from Spectrogon US, Inc. in New Jersey, for example. Other optical bandpass filters of other embodiments may have different transmission curves with different pass bands, different shapes, different materials, and different characteristics (e.g., full width at half maximum 82, center wavelength 84, peak transmission 86, etc.). There are many different optical bandpass filters available from numerous manufacturers. Referring to FIG. 4, the optical bandpass filter 46 of the first embodiment allows a transmittance greater than about 45% for infrared light between about 3360 nm and about 3400 nm to pass therethrough. Another optical bandpass filter (curve not shown) may be used in alternative, for example, that allows a transmittance greater than about 45% for infrared light between about 3350 nm and about 3390 nm to pass therethrough, which may provide similar or essentially the same results as the filter of the first embodiment.

Figure 5:
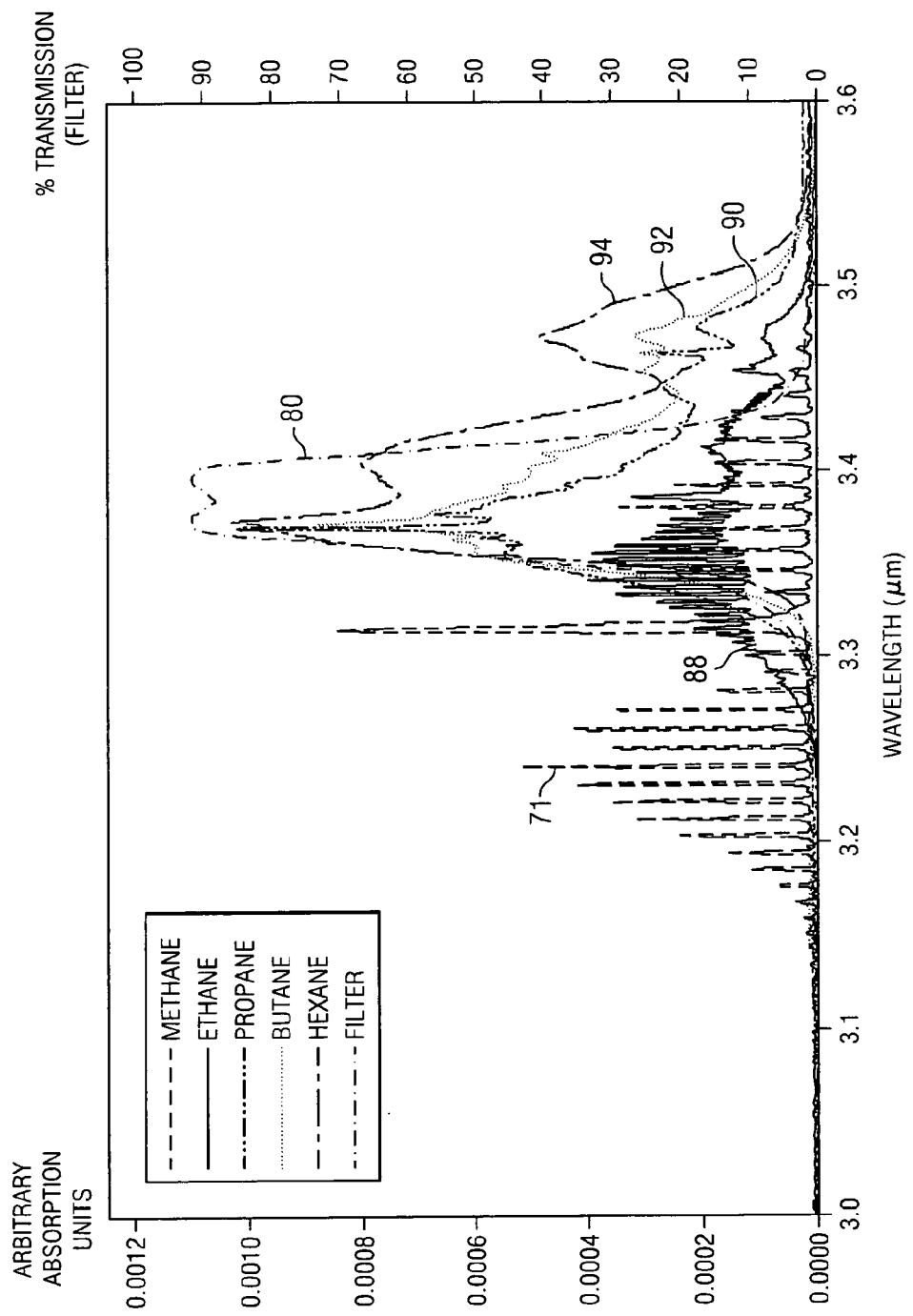
FIG. 5 is an absorption graph for a small set of alkane chemicals with the pass band of the first embodiment transposed thereon.

FIG. 5 is a graph between 3000 nm and 3600 nm showing absorption bands for some common alkane chemicals: methane (71), ethane (88), propane (90), butane (92), and hexane (94), for example. In FIG. 5, the pass band 80 for the filter 46 of the first embodiment has been overlaid with the absorption bands 71, 88, 90, 92, 94. In FIG. 5, note that at least part of the pass band 80 for the optical bandpass filter 46 is located within the first absorption band 71 for methane. The use of this optical bandpass filter 46 in the first embodiment provides a high sensitivity to infrared light being absorbed by methane between about 3200 nm and about 3500 nm (see FIG. 5). Also, note that the pass band 80 for this optical bandpass filter 46 also provides a high sensitivity to infrared light being absorbed by ethane (88), propane (90), butane (92), and hexane (94) between about 3200 nm and about 3500 nm (see FIG. 5). Although an embodiment may be adapted to detect a certain chemical leaking from a component, the same set up may also be useful and capable of detecting a set or group of chemicals, as is the case for the first embodiment of the present invention. Thus, the infrared camera system 22 of the first embodiment is adapted to provide a visible image representing an infrared image of methane, ethane, propane, butane, and/or hexane emanating from a component.

Figure 6:
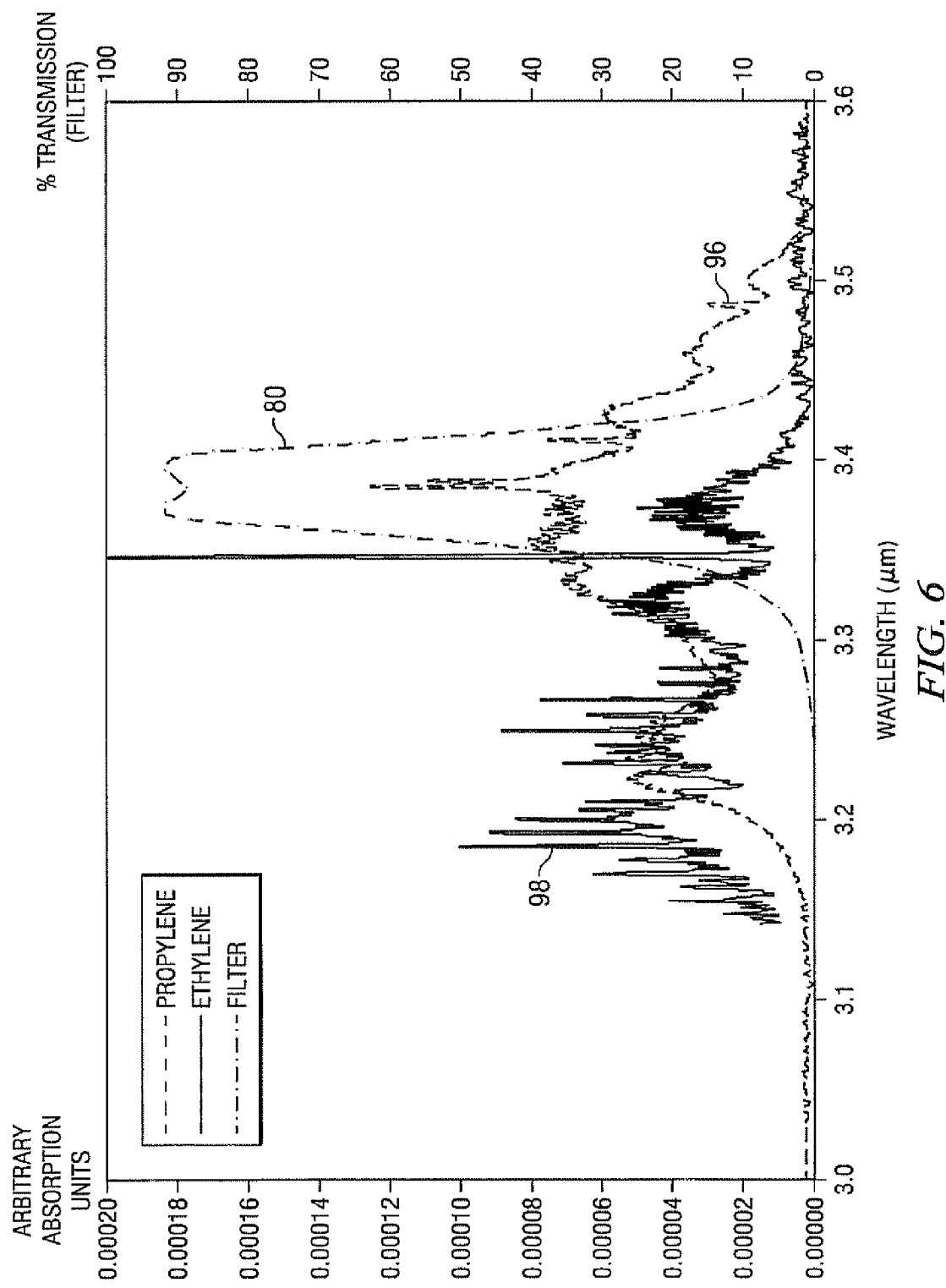
FIG. 6 is an absorption graph for a small set of alkene chemicals with the pass band of the first embodiment transposed thereon.

FIG. 6 is a graph between 3000 nm and 3600 nm showing absorption bands for some common alkene chemicals: propylene (96) and ethylene (98), for example. In FIG. 6 (as in FIG. 5), the pass band 80 for the filter 46 of the first embodiment has been overlaid with the absorption bands of propylene (96) and ethylene (98) located between 3000 nm and 3600 nm. In FIG. 6, note that at least part of the pass band 80 for the optical bandpass filter 46 is located within the absorption bands 96, 98 shown for propylene and ethylene. Thus, the infrared camera system 22 of the first embodiment is also adapted to provide a visible image representing an infrared image of propylene and/or ethylene emanating from a component.

Figure 7:
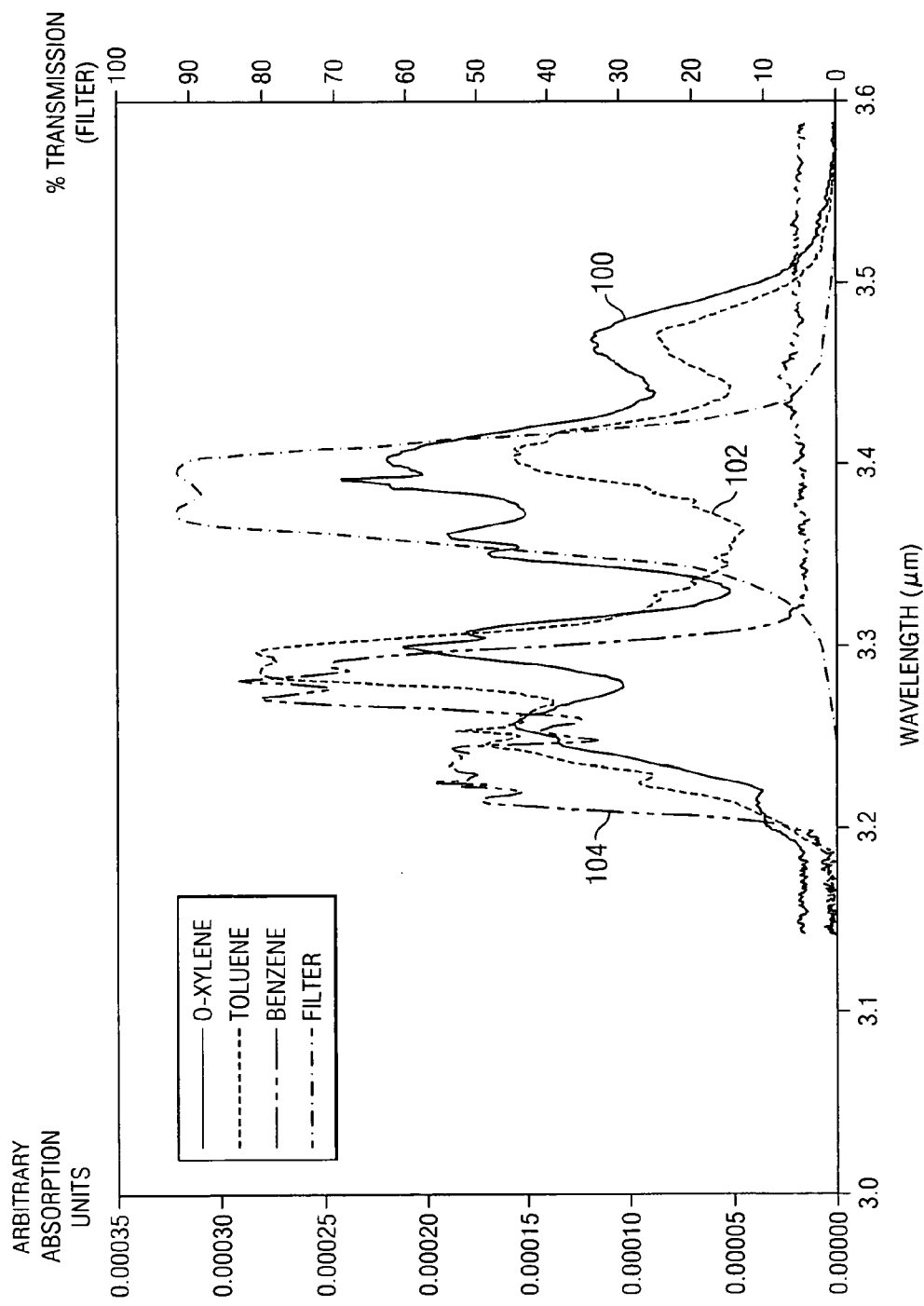
FIG. 7 is an absorption graph for a small set of aromatic chemicals with the pass band of the first embodiment transposed thereon.

FIG. 7 is a graph between 3000 nm and 3600 nm showing absorption bands for some common aromatic chemicals:

o-xylene (100), toluene (102), and benzene (104), for example. In FIG. 7 (as in FIGS. 5 and 6), the pass band 80 for the filter 46 of the first embodiment has been overlaid with the absorption bands of o-xylene (100), toluene (102), and benzene (104) located between 3000 nm and 3600 nm. In FIG. 7, note that at least part of the pass band 80 for the optical bandpass filter 46 is located within the absorption bands 100, 102, 104 shown for o-xylene, toluene, and benzene. Thus, the infrared camera system 22 of the first embodiment is also adapted to provide a visible image representing an infrared image of o-xylene, toluene, and/or benzene emanating from a component.

In other embodiments adapted to visually detect a methane gas leak emanating from a component (and/or some other chemical having an absorption band overlapping or near that of the first absorption band 71 for methane), the optical bandpass filter 46 may have any of a variety of characteristics, including (but not limited to): the pass band of the optical bandpass filter having a center wavelength located between about 3375 nm and about 3385 nm; the optical bandpass filter being adapted to allow a transmittance greater than about 80% of infrared light between about 3365 nm and about 3395 nm to pass therethrough; the pass band of the optical bandpass filter having a center wavelength located between about 3340 nm and about 3440 nm; the pass band of the optical bandpass filter having a center wavelength between about 3360 nm and about 3380 nm; the pass band for the optical bandpass filter being located between about 3100 nm and about 3600 nm; the pass band for the optical bandpass filter being located between about 3200 nm and about 3500 nm; the pass band for the optical bandpass filter being located between about 3300 nm and about 3500 nm; the pass band of the optical bandpass filter having a full width at half maximum transmittance that is less than about 600 nm; the pass band of the optical bandpass filter having a full width at half maximum transmittance that is less than about 400 nm; the pass band of the optical bandpass filter having a full width at half maximum transmittance that is less than about 200 nm; the pass band of the optical bandpass filter having a full width at half maximum transmittance that is less than about 100 nm; the pass band of the optical bandpass filter having a full width at half maximum transmittance that is less than about 80 nm; the optical bandpass filter being adapted to allow a transmittance greater than about 70% at the center wavelength; the pass band for the optical bandpass filter having a center wavelength located within the absorbance band for the chemical; the pass band for the optical bandpass filter having a center wavelength located partially outside of the absorbance band for the chemical; and combinations thereof, for example.

In other embodiments, the optical bandpass filter 46 may comprise two or more optical filters (e.g., in series) located in the refrigerated portion 42 (i.e., cooled filters) to provide the same function as one single bandpass passive filter. For example, a first optical filter (not shown) of the optical bandpass filter 46 may have a high pass filter characteristic to allow infrared light greater than about 3100 nm to pass therethrough, and a second optical filter (not shown) of the optical bandpass filter 46 may have a low pass filter characteristic to allow infrared light less than about 3600 nm to pass therethrough, which together provide an effective pass band located between about 3100 nm and 3600 nm.

An embodiment of the present invention may be adapted to visually detect a leak of any of a wide variety of chemicals (or evaporated gases therefrom), including (but not limited to): hydrocarbon; methane; ethane; propane; butane; hexane; ethylene; propylene; acetylene; alcohol; ethanol; methanol; xylene; benzene; formaldehyde; 1,2 butadiene; 1,3 butadiene; butadiyne; acetone; gasoline; diesel fuel; petroleum; petrochemicals; petroleum by-product; volatile organic compound; volatile inorganic compound; crude oil products; crude oil by-products; and combinations thereof, for example. FIGS. 8-19 illustrate some example absorption bands (among many) for some example chemicals (among many) that may be detected while leaking from a component using an embodiment of the present invention, and some example pass bands (among many) for the optical bandpass filter 46 that may be used in an embodiment of the present invention.

In FIGS. 8-19, the pass band 80 for the optical bandpass filter 46 is schematically represented by a rectangular box to show its approximate placement relative to the absorption bands of the chemicals. As is well known by those of ordinary skill in the art, the actual pass band for an optical bandpass filter will typically have some sort of curve shape (often a bell-curve shape) rather than being rectangular. The rectangular shape is merely used for schematic illustration, as the actual pass band (and the actual transmission curve) for an optical bandpass filter 46 of an embodiment may have any of a wide variety of shapes (symmetry, asymmetry, height, slope, skew, full width at half maximum, peak transmission, etc.).

Figure 8:
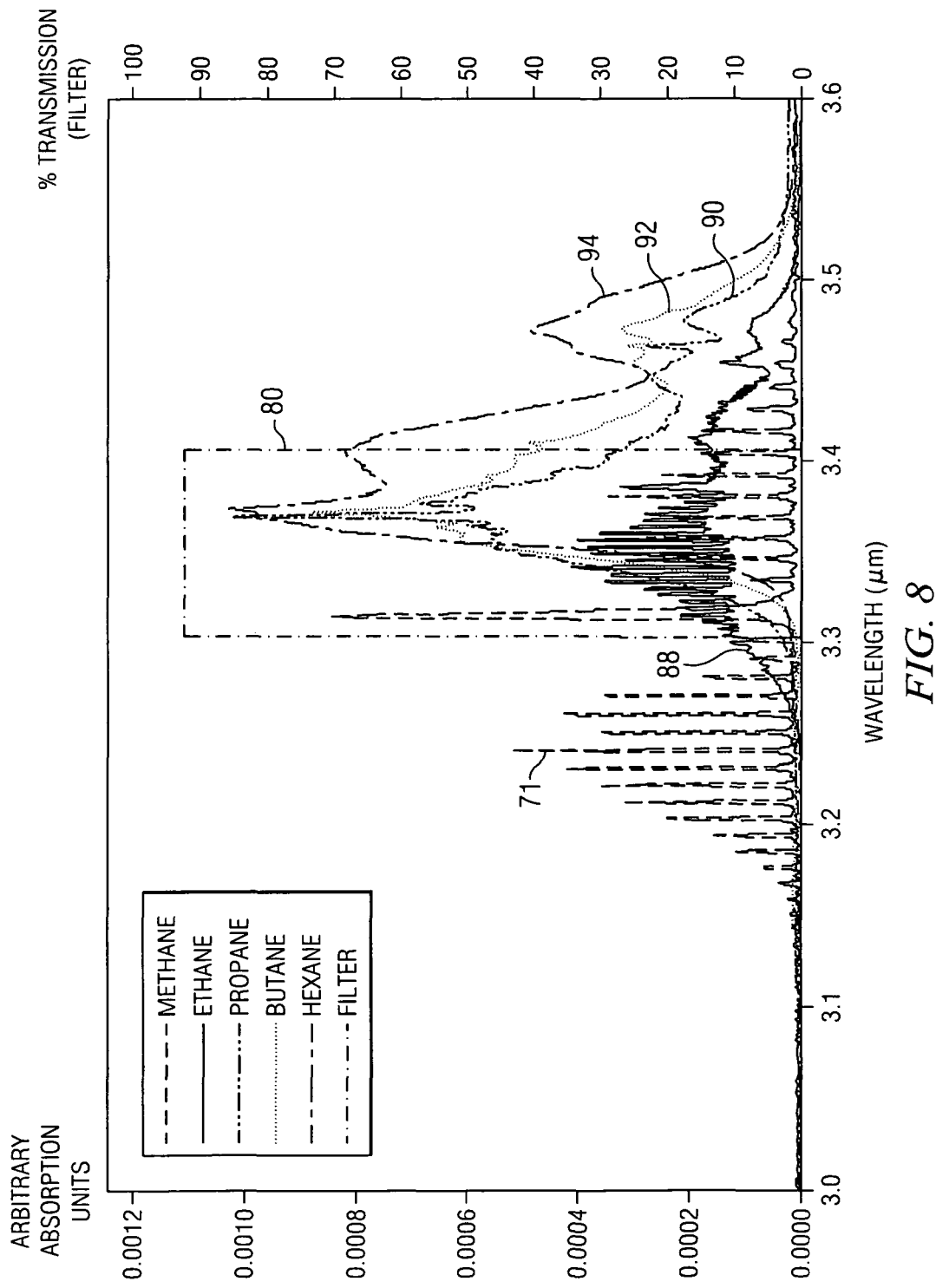
FIG. 8 is an absorption graph for a small set of alkane chemicals with a schematic representation of a pass band for a second embodiment transposed thereon.
Figure 9:
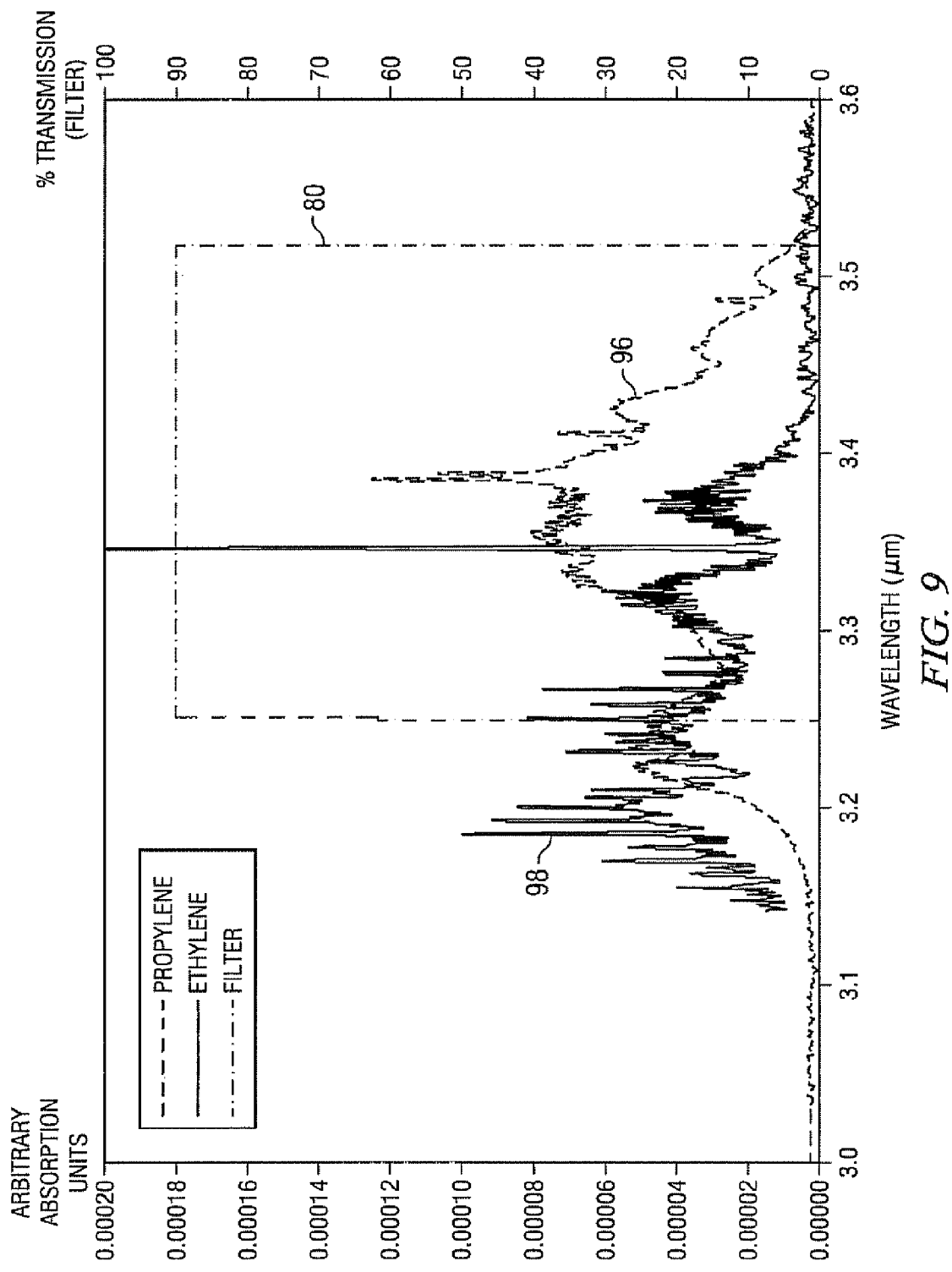
FIG. 9 is an absorption graph for a small set of alkene chemicals with a schematic representation of a pass band for a third embodiment transposed thereon.
Figure 10:
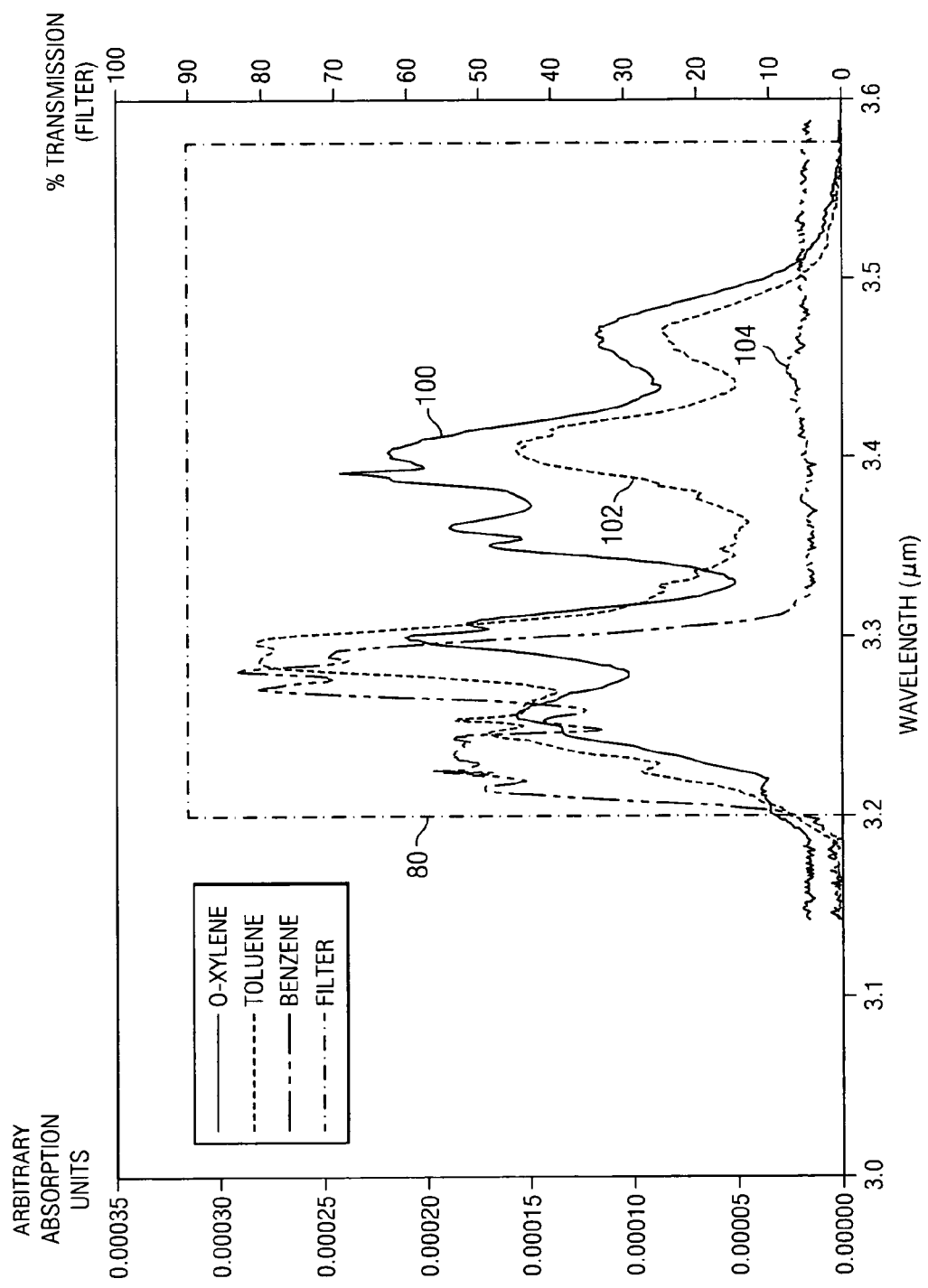
FIG. 10 is an absorption graph for a small set of aromatic chemicals with a schematic representation of a pass band for a fourth embodiment transposed thereon.

FIG. 8 shows some absorption bands 71, 88, 90, 92, 94 for the same alkanes from FIG. 5 from 3000 nm to 3600 nm. In FIG. 8, the pass band 80 for the optical bandpass filter 46 of a second embodiment is located between about 3300 nm and about 3400 nm with a full width at half maximum less than about 100 nm, for example. FIG. 9 shows some absorption bands 96, 98 for the same alkenes from FIG. 6 from 3000 nm to 3600 nm. In FIG. 9, the pass band 80 for the optical bandpass filter 46 of a third embodiment is located between about 3250 nm and about 3510 nm with a full width at half maximum less than about 250 nm, for example. FIG. 10 shows some absorption bands 100, 102, 104 for the same aromatics from FIG. 7 from 3000 nm to 3600 nm. In FIG. 10, the pass band 80 for the optical bandpass filter 46 of a fourth embodiment is located between about 3200 nm and about 3580 nm with a full width at half maximum less than about 350 nm, for example.

Figure 11:
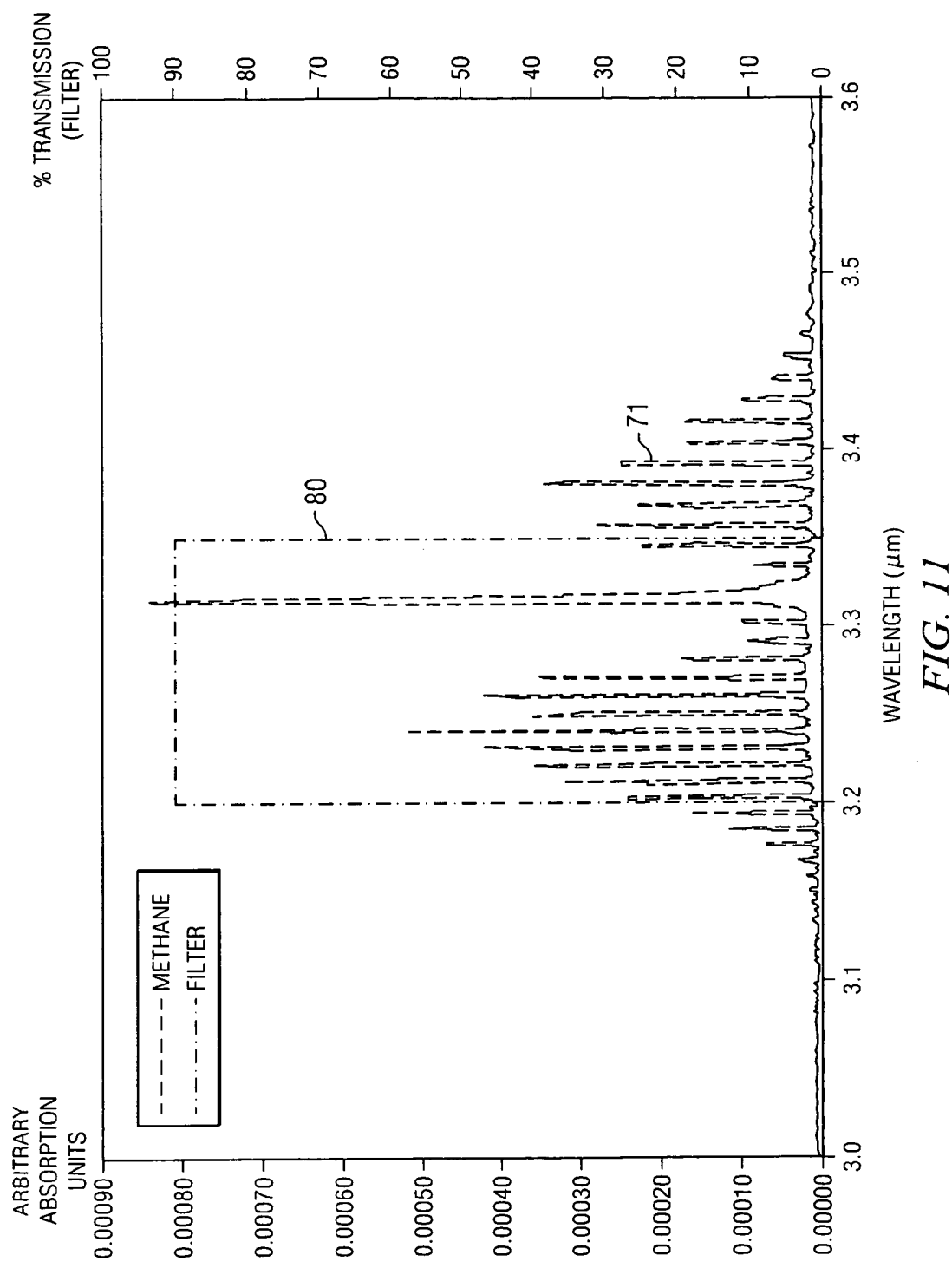
FIG. 11 is an absorption graph for methane with a schematic representation of a pass band for a fifth embodiment transposed thereon.
Figure 12:
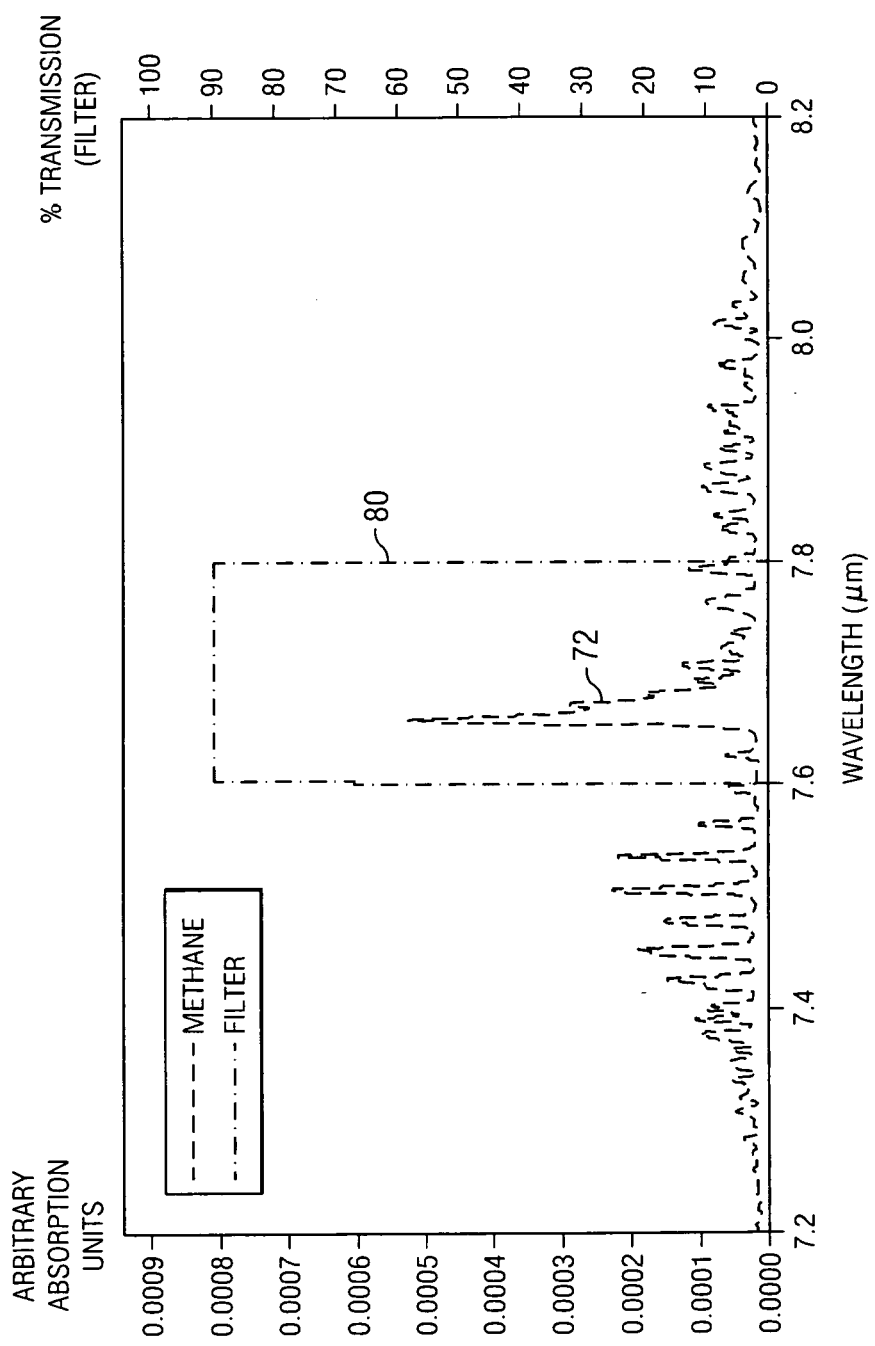
FIG. 12 is an absorption graph for methane with a schematic representation of a pass band for a sixth embodiment transposed thereon.

FIG. 11 shows the first absorption band 71 for methane (see e.g., FIG. 3A). In FIG. 11, the pass band 80 for the optical bandpass filter 46 of a fifth embodiment is located between about 3200 nm and about 3350 nm with a full width at half maximum less than about 150 nm, for example. Hence, the fifth embodiment is adapted to visually detect methane leaks emanating from a component. FIG. 12 shows the second absorption band 72 for methane (see e.g., FIG. 3A). In FIG. 12, the pass band 80 for the optical bandpass filter 46 of a sixth embodiment is located between about 7600 nm and about 7800 nm with a full width at half maximum less than about 200 nm, for example. Thus, the sixth embodiment is also adapted to visually detect methane leaks emanating from a component.

Figure 13:
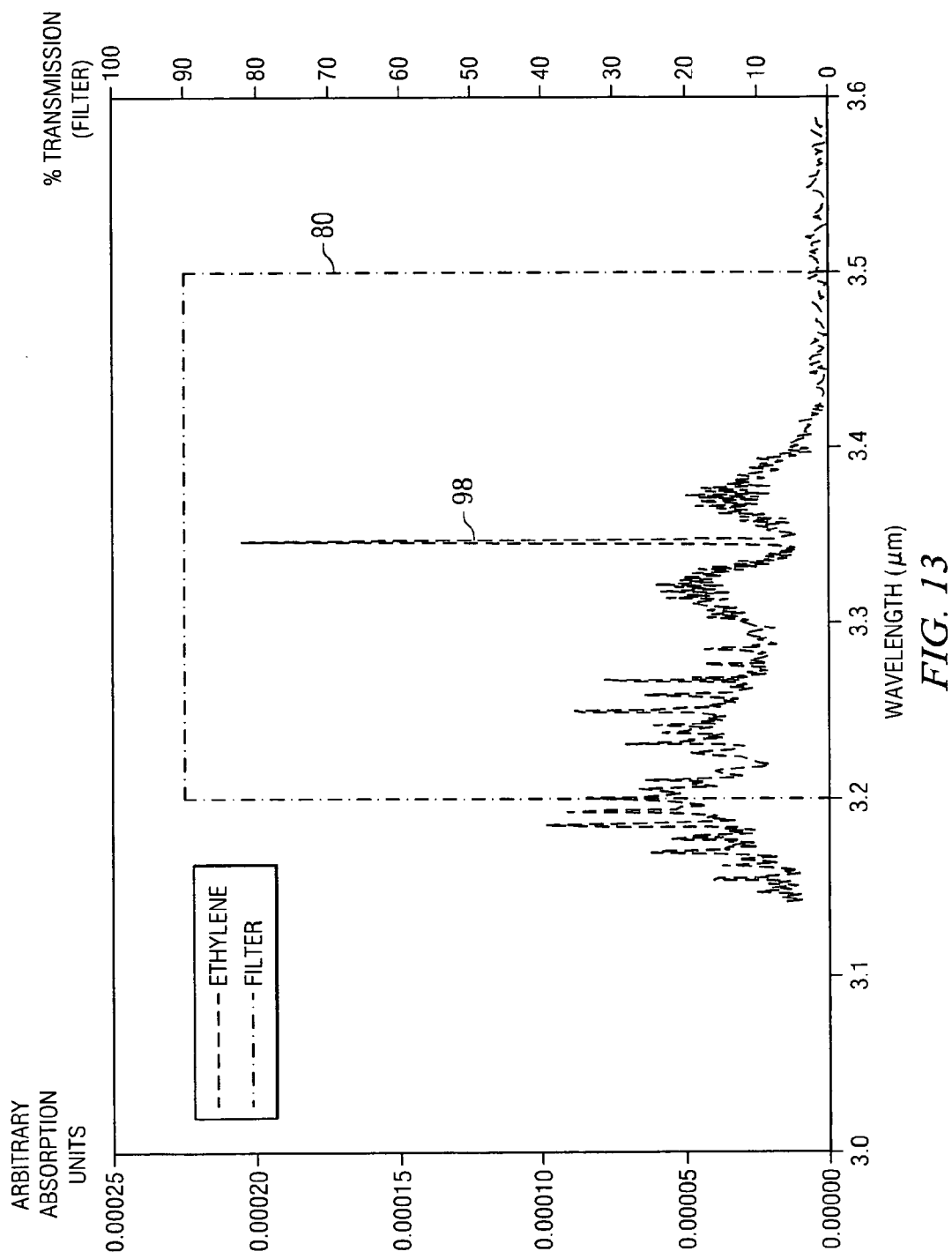
FIG. 13 is an absorption graph for ethylene with a schematic representation of a pass band for a seventh embodiment transposed thereon.
Figure 14:
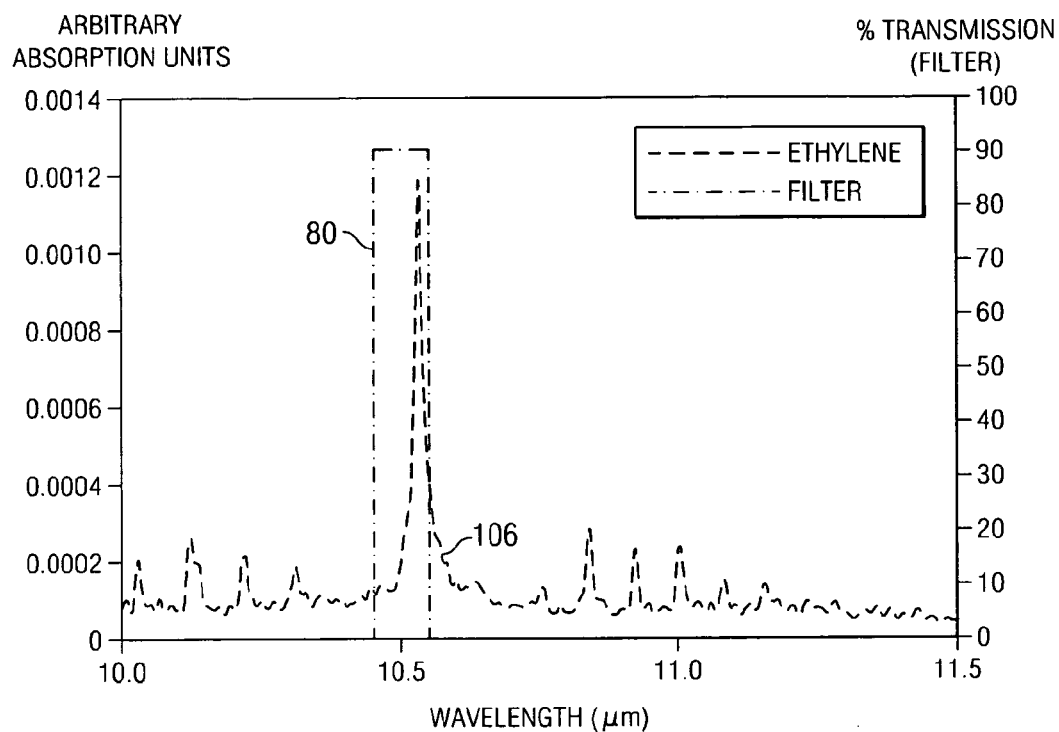
FIG. 14 is an absorption graph for ethylene with a schematic representation of a pass band for an eighth embodiment transposed thereon.

FIG. 13 shows an absorption band 98 for ethylene located between about 3100 nm and about 3500 nm. In FIG. 13, the pass band 80 for the optical bandpass filter 46 of a seventh embodiment is located between about 3200 nm and about 3500 nm with a full width at half maximum less than about 300 nm, for example. Hence, the seventh embodiment is adapted to visually detect ethylene leaks emanating from a component. FIG. 14 shows another absorption band 106 for ethylene, which is located between about 10000 nm and about 11500 nm. In FIG. 14, the pass band 80 for the optical bandpass filter 46 of an eighth embodiment is located between about 10450 nm and about 10550 nm with a full width at half maximum less than about 100 nm, for example. Thus, the eighth embodiment is also adapted to visually detect ethylene leaks emanating from a component.

Figure 15:
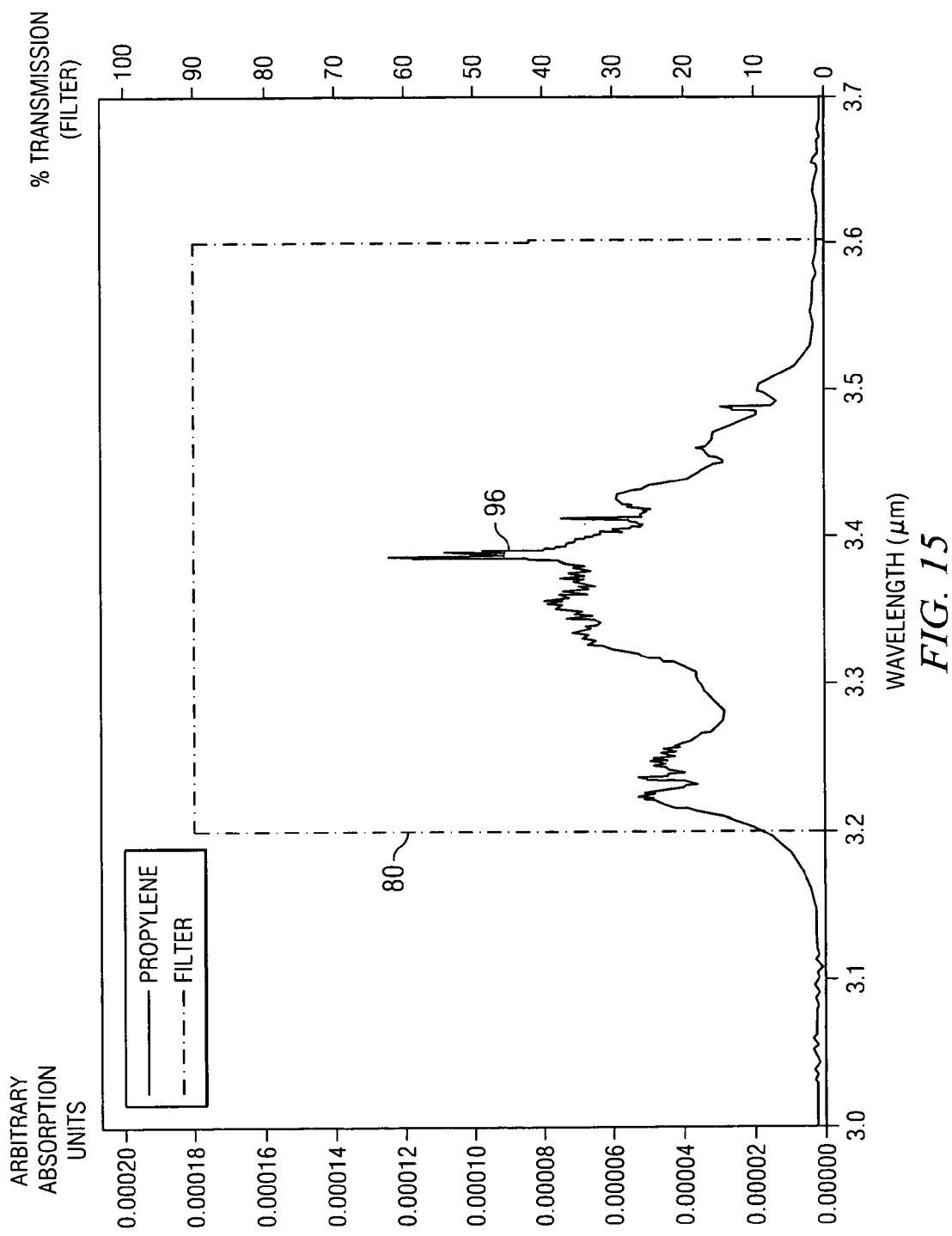
FIG. 15 is an absorption graph for propylene with a schematic representation of a pass band for a ninth embodiment transposed thereon.
Figure 16:
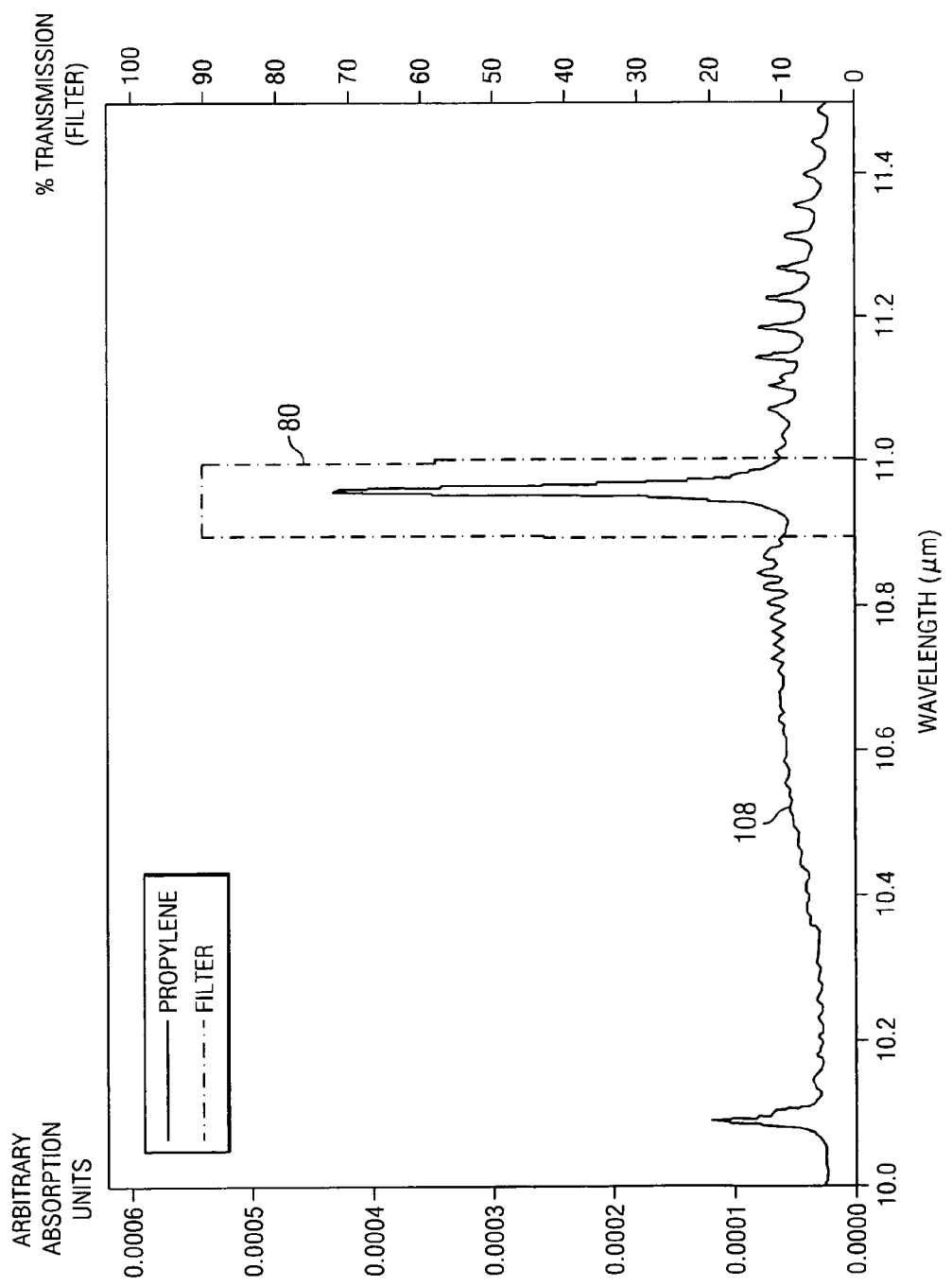
FIG. 16 is an absorption graph for propylene with a schematic representation of a pass band for a tenth embodiment transposed thereon.

FIG. 15 shows an absorption band 96 for propylene located between about 3100 nm and about 3600 nm. In FIG. 15, the pass band 80 for the optical bandpass filter 46 of a ninth embodiment is located between about 3200 nm and about 3600 nm with a full width at half maximum less than about 400 nm, for example. Hence, the ninth embodiment is adapted to visually detect propylene leaks emanating from a component. FIG. 16 shows another absorption band 108 for propylene, which is located between about 10000 nm and about 11500 nm. In FIG. 16, the pass band 80 for the optical bandpass filter 46 of a tenth embodiment is located between about 10900 nm and about 11000 nm with a full width at half maximum less than about 100 nm, for example. Thus, the tenth embodiment is also adapted to visually detect propylene leaks emanating from a component.

Figure 17:
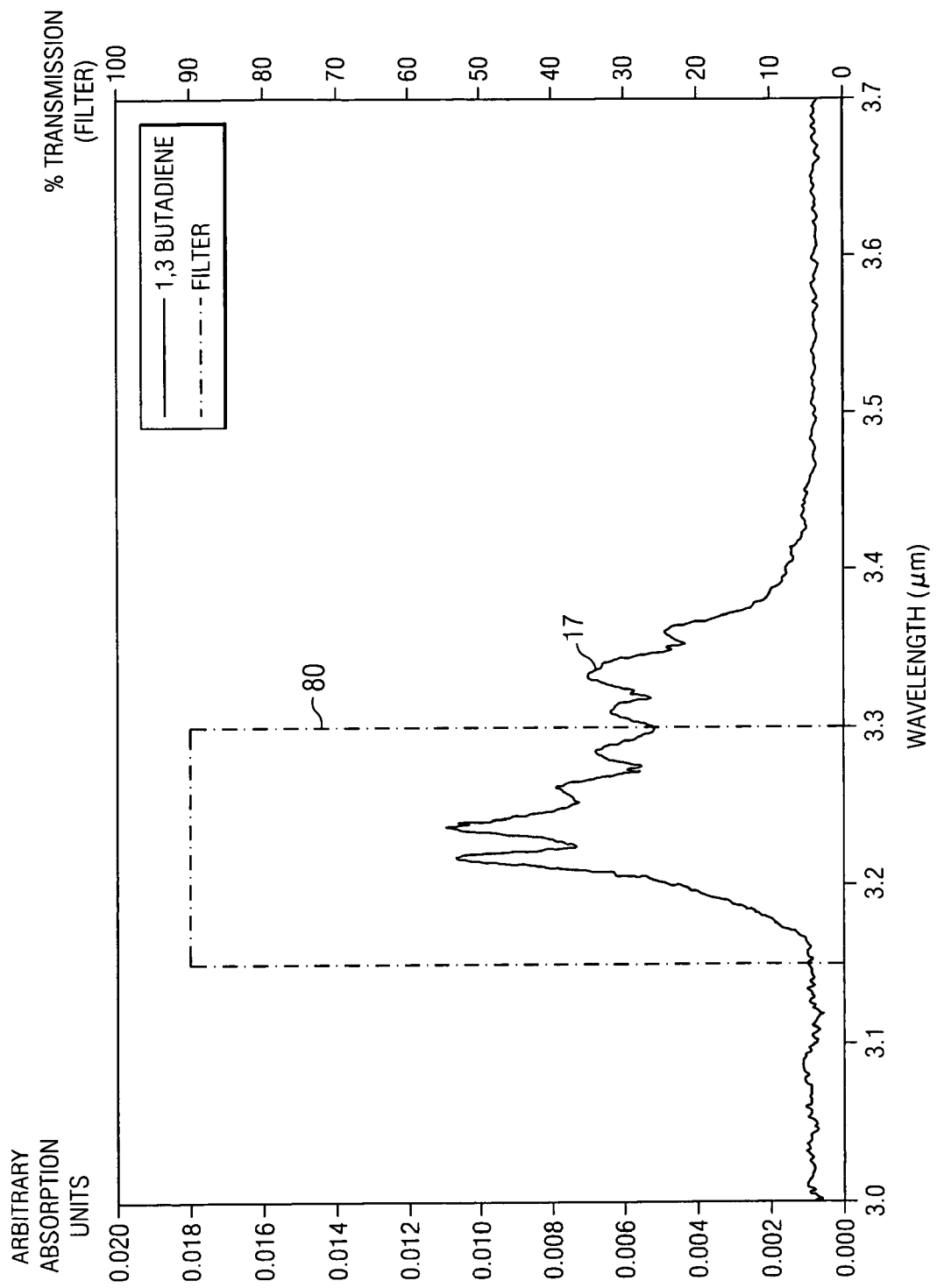
FIG. 17 is an absorption graph for 1,3 butadiene with a schematic representation of a pass band for an eleventh embodiment transposed thereon.

FIG. 17 shows an absorption band 17 for 1,3 butadiene located between about 3100 nm and about 3500 nm. In FIG. 17, the pass band 80 for the optical bandpass filter 46 of an eleventh embodiment is located between about 3150 nm and about 3300 nm with a full width at half maximum less than about 150 nm, for example. Hence, the eleventh embodiment is adapted to visually detect 1,3 butadiene leaks emanating from a component. Note that in another embodiment (not shown), the pass band of the eleventh embodiment may be located between about 3200 nm and about 3400 nm, for example, as another variation. If it is of particular interest to detect leaks of a certain chemical (or set of chemicals), it is preferred to have the pass band 80 overlaying the absorption band where the area under the absorption band is higher to provide better detection sensitivity. The width of the pass band 80 may or may not be critical for a given chemical, depending largely upon the characteristic shape of that chemical's absorption band (e.g., width along wavelength axis, height along absorption axis).

Figure 18:
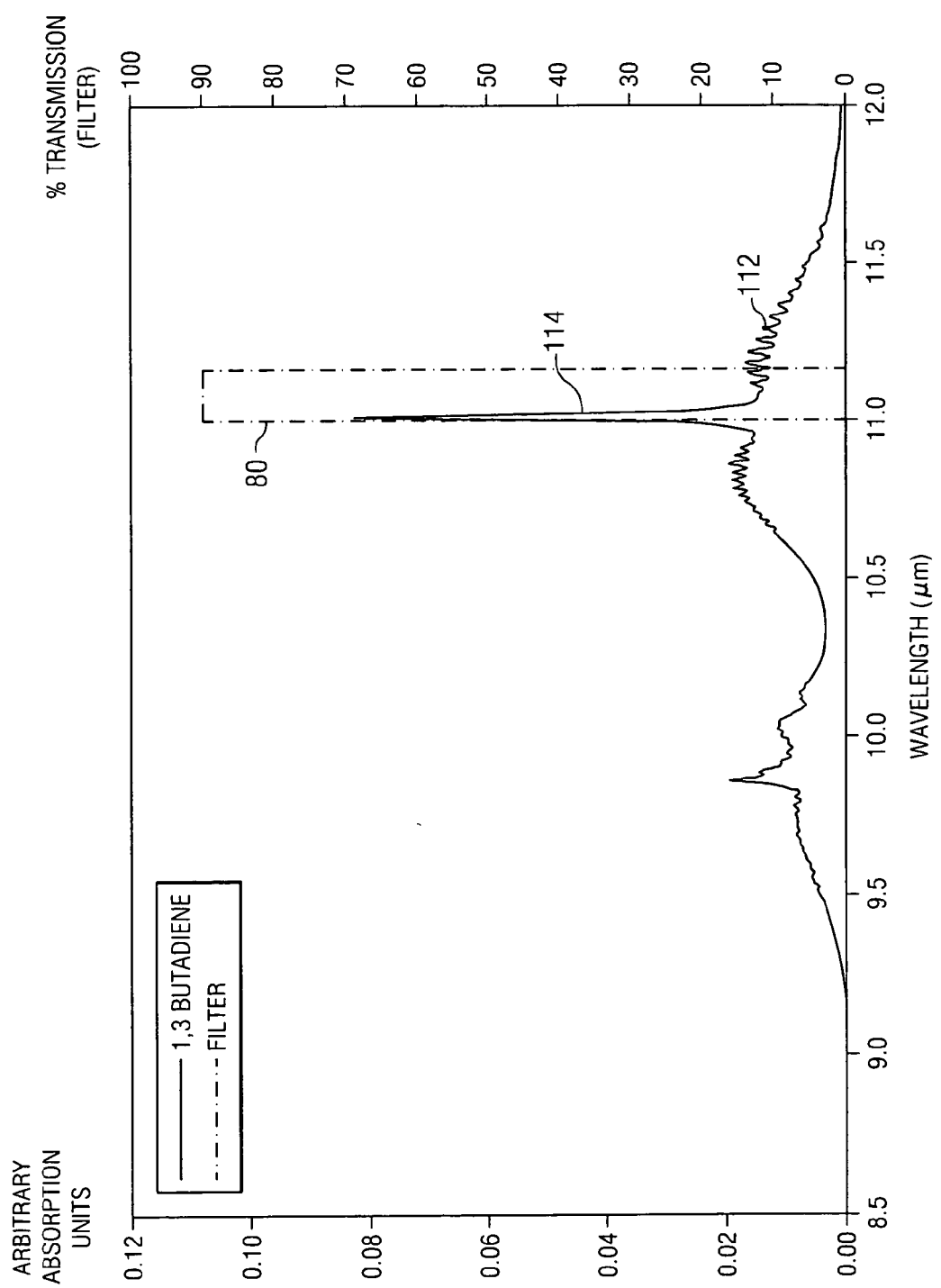
FIG. 18 is an absorption graph for 1,3 butadiene with a schematic representation of a pass band for a twelfth embodiment transposed thereon.

FIG. 18 shows another absorption band 112 for 1,3 butadiene, which is located between about 9000 nm and about 12000 nm. In FIG. 16, the pass band 80 for the optical bandpass filter 46 of a twelfth embodiment is located between about 9000 nm and about 12000 nm with a full width at half maximum less than about 150 nm, for example. Thus, the twelfth embodiment is also adapted to visually detect 1,3 butadiene leaks emanating from a component. Note that the pass band 80 in FIG. 18 is not centered on the largest peak 114 of the absorption band 112. In another embodiment (not shown), it may be preferred to have the pass band 80 centered at or closer to the largest peak 114 of the absorption band 112.

Figure 19:
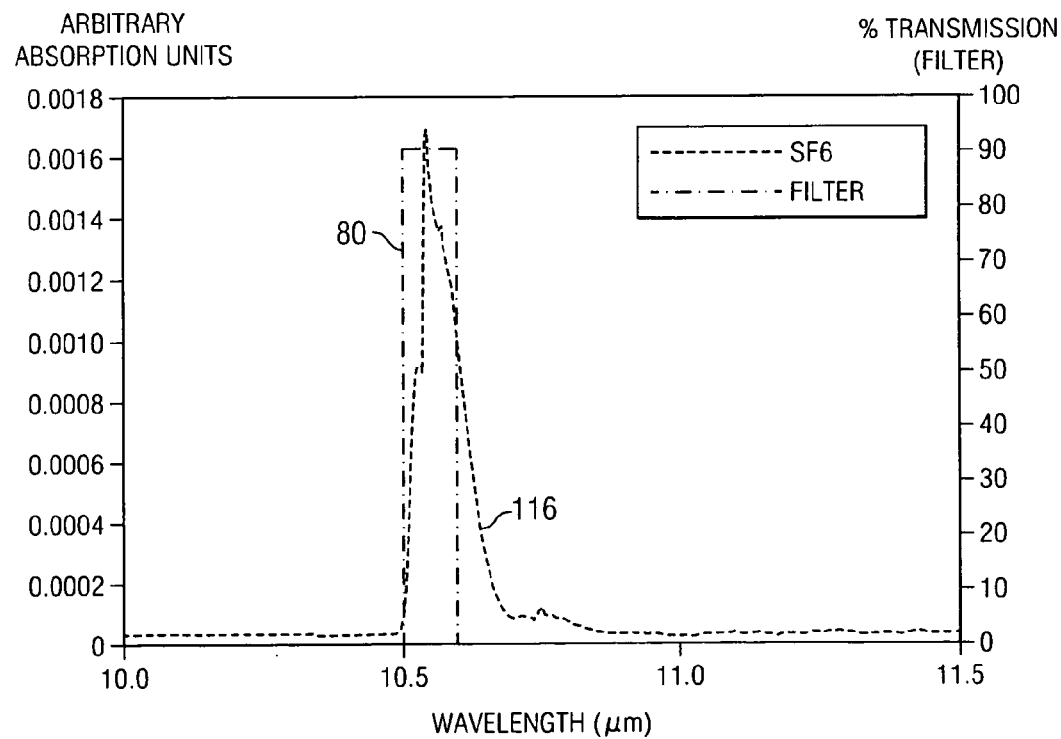
FIG. 19 is an absorption graph for sulfur hexafluorine with a schematic representation of a pass band for a thirteenth embodiment transposed thereon.

FIG. 19 shows an absorption band 116 for sulfur hexafluoride ($SF_6$) located between about 10000 nm and about 11500 nm. In FIG. 19, the pass band 80 for the optical bandpass filter 46 of a thirteenth embodiment is located between about 10500 nm and about 10600 nm with a full width at half maximum less than about 100 nm, for example. Thus, the thirteenth embodiment is adapted to visually detect $SF_6$ leaks emanating from a component. Sulfur hexafluoride is often used in switching gear for electrical equipment and its emissions are harmful to the environment. Hence, an embodiment of the present invention may be used to visually detect $SF_6$ leaks emanating from electrical equipment, for example.

Figure 20:
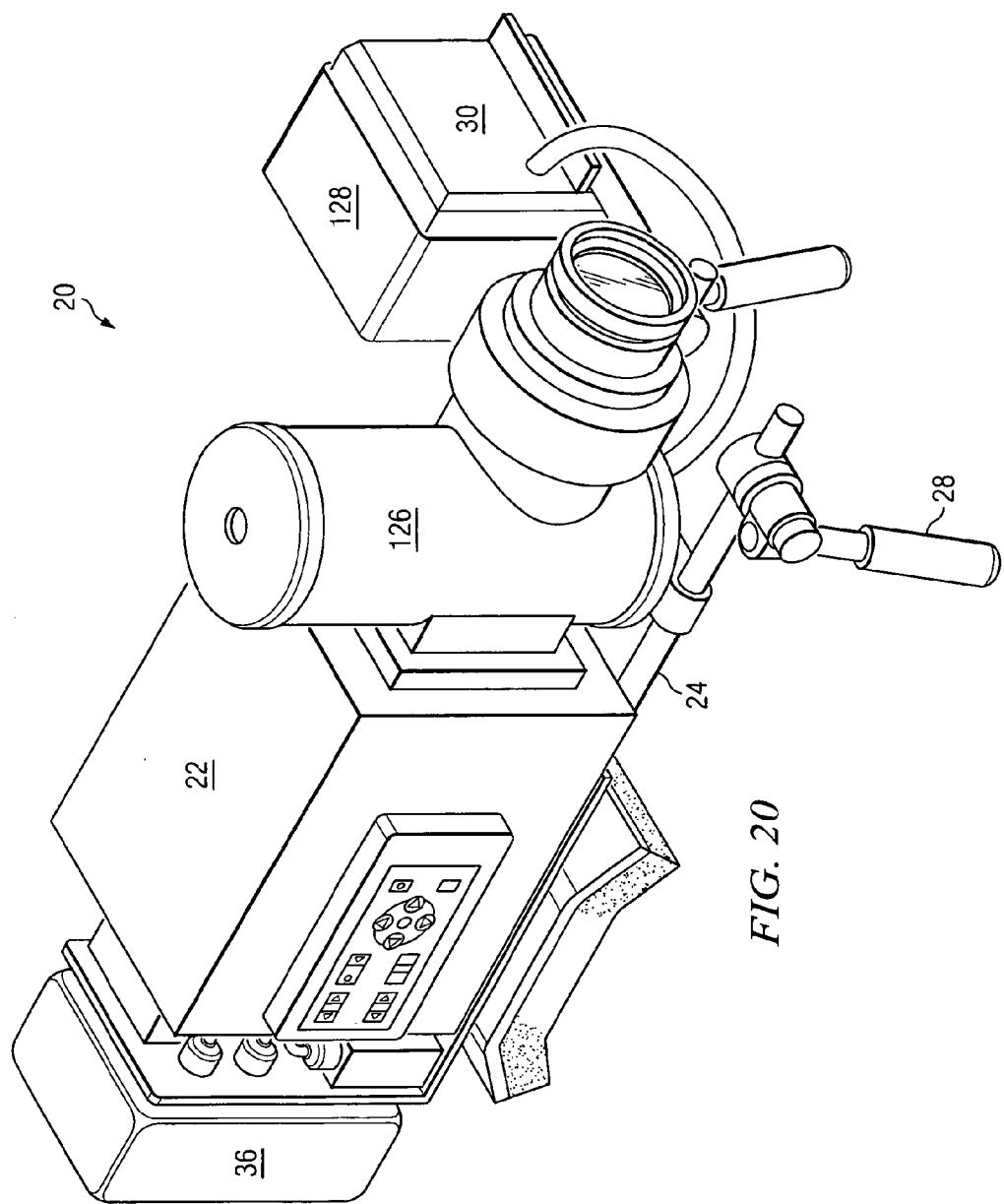
FIG. 20 is perspective view of a chemical leak detection system of a fourteenth embodiment.

FIG. 20 shows a fourteenth embodiment of the present invention. In the fourteenth embodiment, the refrigeration system 60 of the infrared camera system 22 has a chamber 126 adapted to retain liquid nitrogen therein. The liquid nitrogen has thermal communication with the refrigerated portion 42 to cool the infrared sensor device 44 and optical bandpass filter 46 located therein. For the fourteenth embodiment, a currently preferred infrared camera system (22) is the InSb Laboratory Camera by Indigo System, Inc. of California, particularly when made portable (as shown in FIG. 20). The frame 24, battery 36, and display screen 30 may be the same on the fourteenth embodiment (FIG. 20) as that of the first embodiment (FIG. 1). To provide for better viewing of the display screen 30 in a bright environment, a shroud, hood, or visor may be provided around the display screen 30. For example, the fourteenth embodiment shown in FIG. 20 has a light shield 128 located proximate to the screen 30 for partially shielding the screen 30 from ambient light. During use, an inspector may place his face up to or against the edge of the shroud to shield the environmental light from the display screen 30 and allow the inspector to view the screen with the darkened enclosure formed.

An embodiment of the present invention may be used to inspect any of a wide variety of components having the chemical (or chemicals) of interest therein, including (but not limited to): a pipe, a compressor, an engine, a valve, a container, a tank, a switch, a reservoir, a fitting, a connector, a hose, a flare, an exhaust outlet, a machine, a vent for a blow-off valve, and combinations thereof, for example. Some example uses of embodiments of the present invention will be described next.

An embodiment of the present invention may be used to visually detect the evaporation (i.e., fumes) of petroleum products leaking from a component, such as a valve or pipe fitting. An advantage of an embodiment of the present invention over prior methods of detecting leaks (e.g., flame pack ionizer, sniffer device) is that the inspector can actually see the leak flowing by the visible image (representing the infrared image) provided by the infrared camera system 22. Using a sniffer device, the sensor has to be within the flow stream to detect it, which requires close proximity and thorough scanning to cover an entire component or area. Using an embodiment of the present invention, an inspector can visually scan a large area in a much shorter period of time, and the inspector can do so from a distance. Thus, the inspector may not need to climb on and around equipment, which may be dangerous to the inspector. Also, pipes needing inspection are often located overhead along a roof, which is difficult to inspect with a sniffer device. But with an embodiment of the present invention, an inspector may stand below the pipes and perform the visual inspection using the infrared camera system 22 from the ground (from a distance).

Also, an inspector may combine the use of an embodiment of the present invention with other inspection methods. For example, after an inspector locates a leak visually with the infrared camera system 22 of an embodiment, the inspector could then do a further analysis of the leak using other measurement tools.

In a first method of using an embodiment of the present invention, an embodiment of the present invention (e.g., first embodiment) is used to visually inspect a natural gas (methane) regulator station 120. Usually, such regulator stations are enclosed within the boundary of a fence 122. As shown in FIG. 21, an inspector 124 using an embodiment of the present invention may inspect the regulator station 120 from a location outside of the boundary defined by the fence 122, even though the regulator station 120 is located within the boundary defined by the fence 122. If the fence 122 cannot be seen through, as with a chain-link fence or a steel tubing fence, the inspector 124 may be able to visually inspect the regulator station 120 over the fence 122. For example, the inspector 124 could stand on an object (e.g., truck bed). As another alternative, an inspector 124 could be lifted by a boom on a boom-truck, for example. Also, the inspector 124 may perform the inspection within the fence boundary 122.

For most methods of using an embodiment of the present invention to visually detect a leak of a chemical (or chemicals) emanating from a component, the following steps will be performed. An inspector aims the infrared camera system 22 toward the component or components of interest. Infrared images of the component and background enter the camera system 22 via the lens assembly 40 (at least one lens 38) (see e.g., camera system 22 in FIG. 2). The infrared image passes through the optical bandpass filter 46 on its way to the infrared sensor device 44. The infrared image is filtered by the optical bandpass filter 46 in accordance with the characteristics of the filter 46 (i.e., its pass band 80). The filtered infrared image is then received by the infrared sensor device 44, which converts the filtered infrared image to an electrical signal representing the filtered infrared image. This electrical signal is then electronically processed, within the camera system 22 (see e.g., FIG. 2) and/or externally by another device outside of the camera system 22, to provide a visible image representing the filtered infrared image. This visible image may be viewed in real time by the inspector, viewed by another person at another location (e.g., remotely located), recorded, transmitted to another device, transmitted to another location, or combinations thereof, for example.

In a method of the present invention, an inspector may obtain images and evaluate the images while performing the inspection. In another method, the inspector may do the same, and in addition, the images may be recorded and reviewed a second time. The second review may be performed by the same inspector, another person, or by a computer using image recognition software. The second review may find anything missed in the original survey. The ability to have a second review is not available with many conventional ways of doing leak surveys (e.g., using flame-packs) because a focused visual image of the inspection is not provided. Thus, a better leak survey requiring the same time and money (or less) may be performed using a method of the present invention, plus a visual record of the leak may be stored and may be viewed numerous times.

An advantage of an embodiment of the present invention is that it may allow the recording of the images obtained during the visual inspection. Such recordings may be useful in a number of ways. The recorded image obtained in the field may be transmitted (e.g., in real time or later) to a reviewer (person or computer system) at another location or a remote location. Sometimes in the field where bright conditions exist outside, for example, it may be difficult for the inspector to see small details on the video monitor or display screen. Also, the inspection conditions may not be conducive to a careful study of the image during the inspection. Thus, a reviewer located in a dark and stable environment may provide a better review of the images obtained by the system. The images may be recorded by a device attached to the infrared camera system, recorded at a remote location after being transmitted, or recorded by a separate device not attached to the infrared camera system 22, for example. An image may be transmitted from the camera system 22 to another device (which may or may not be remotely located) by any of a wide variety of communication means, including (but not limited to): a cable, a wire, between wireless communication devices, via a network connection, via the Internet, or combinations thereof, for example. The images provided by the infrared camera system may be recorded continuously during an inspection and/or they may be recorded as desired over any period of time.

Referring to FIG. 21, note that a video recording device is located in a carrying case separate from the infrared camera system. In other embodiments of the present invention, other components of the system may be separate from the infrared camera system (e.g., carried in a backpack). This may be preferred so that the camera system may be lighter and held easier. An embodiment is contemplated where most of the system components are located in a back pack or some other carrying case (e.g., case with wheels and handle) so that the camera portion having the lens, optical bandpass filter, and infrared sensors may be located in a smaller hand held unit. Such a hand held unit may include a small flat panel display screen, for example. It is also contemplated that the visible images from the camera may be displayed to an inspector using a system that projects the images directly into one or more of the inspector's eyes or onto an interior surface of a eyepiece or eyeglasses. One of ordinary skill in the art will realize many different types and sizes of display screens or projectors that may be incorporated into or used for an embodiment of the present invention.

It is also contemplated that an embodiment of the present invention may be made intrinsically safe to allow for greater flexibility and usages of the system for performing inspections. Also, providing an embodiment that incorporates an intrinsically safe infrared camera system may provide the advantage of entering plants for performing inspections without the need for a hot work permit to be issued and/or without the need for other safety precautions normally associated with the use of a non-intrinsically safe inspection system.

It is further contemplated that an embodiment of the present invention may incorporate a halogen light (e.g., attached to the camera system or separately provided) to provide a greater thermal contrast for the camera system using the heat radiated by the halogen light to change the temperature of the background slightly. It may be useful to use the halogen light on an as needed basis to get a more detailed image (higher sensitivity or better image resolution) of a leak after it is located (such as for making a recording of the leak).

The visual identification of a leak may be performed at another location remote from the infrared camera system and/or remote from the leak location, e.g., while viewing a recording of the images, while viewing an image transmitted to the remote location, or combinations thereof, for example. As an example, an inspection team flying over a transmission line in a helicopter (discussed further below) may be concentrating on obtaining a good image of the transmission line and precisely following GPS coordinates of the transmission line. While in a helicopter, it may be difficult for the inspection team to concentrate on reviewing the images obtained during the inspection process. The visual images obtained by the infrared camera system may be recorded for and/or transmitted to a reviewer. The reviewer may then carefully review the images to look for leaks. Such review may be performed in real-time, which would allow the reviewer to communicate with and instruct the inspectors to go back to a suspect location for a confirmation (i.e., hovering over a certain location and obtaining more images of a single location). Or if the visual inspections are recorded, a reviewer may study the inspection images at a later time. Hence, one of the members of the inspection team may later sit down in an environment more conducive to studying the images to provide the review of the images. Then, if needed or desired, a closer or more lengthy inspection of suspect locations may be performed later.

Government safety regulations and rules typically require that gas or petroleum product transmission lines and distribution lines be inspected at certain regular intervals. If a company does not comply with such rules and regulations, the company may be charged steep fines. Also, if there is some type of accident or incident where a leaking or ruptured line causes an explosion or fire, the company will want to provide evidence that they were diligent and not negligent in performing an inspection of that line. Hence, another benefit of being able to record a focused image of the visual inspection is the ability to have a record of the inspection. In an embodiment of the present invention, GPS coordinates, a date stamp, and/or a time stamp may be recorded onto or embedded within the recorded images of the visual inspection. This will provide evidence that an inspection was performed for a particular location at a particular date and time. Such records may be stored (in analog or digital format) on some type of storage medium (e.g., video tape, CD, DVD, database, hard drive, etc.) for future reference.

In a preferred embodiment and/or method of the present invention, inspection information may be displayed and or recorded along with the recording/displaying of the visible image representing the filtered infrared image. The inspection information may include any relevant information desired, including (but not limited to): inspection location name, inspection location address, component name, component identification information, global positioning coordinates, a date, a time of day, an inspector's name, an inspection company's name, one or more camera system setting values, or combinations thereof, for example. Also, voice notes may be recorded onto or along with the images on a medium (e.g., voice notes recorded on a video of inspection). Such inspection information may be embedded within the visible image or may be recorded and tracked separately (e.g., in a separate file, as a header file, etc.).

Figure 22:
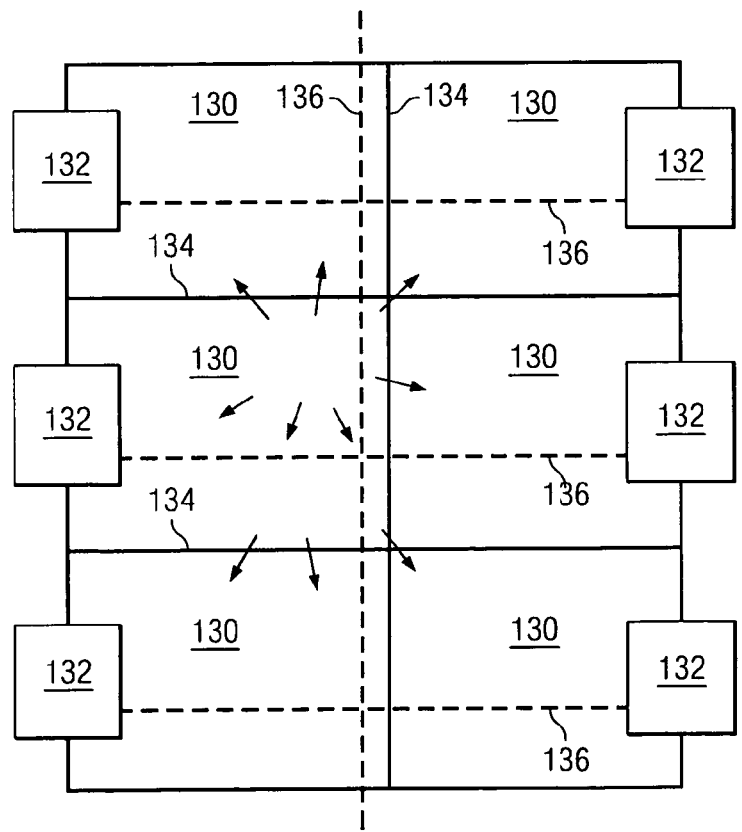
FIG. 22 illustrates a use of an embodiment of the present invention to inspect multiple yards from a single yard.

In a second method of the present invention, an embodiment of the present invention may be used to inspect numerous fenced yards 130 from a single location, from outside the yards 130, and/or from a single yard 130. FIG. 22 shows a housing configuration found in many neighborhoods, where there is no alley behind the houses 132. Instead, only a fence 134 may separate two or more adjacent backyards 130. In FIG. 22, an underground natural gas distribution line 136 is shown in dashed lines, which run across numerous backyards 130. Using conventional leak survey techniques, an inspector would need to enter each backyard 130 to inspect the line in all six of the yards 130 shown in FIG. 22. However, because a leak may be detected visually using an embodiment of the present invention, an inspector may enter only one backyard 130 and see into each of the adjacent yards 130 (as indicated by the arrows in FIG. 22). Thus, only one customer needs to be disturbed for the inspection, rather than six. Also, an inspector may attach the infrared camera system 22 to a boom on a truck, or he may be standing in the boom holding the camera system 22, located at an end of a street or in an alley to obtain visual access to numerous backyards 130. Thus, using an embodiment of the present invention, multiple backyards may be surveyed for line leaks visually using an infrared camera system 22 from a single location (e.g., from a single backyard 130 looking over the fences 134, or from a boom).

Many residential meters for natural gas are located next to a house (e.g., between houses), remote from where a vehicle may drive. Such distribution lines must be periodically tested for leaks. In such cases, using a conventional method of leak surveying, the inspector typically walks to each meter to perform the leak survey. In a third method of the present invention, such meters and distribution lines may be surveyed visually using an infrared camera system from a vehicle. For example, an inspector may aim an infrared camera system at the distribution lines while driving past each home without leaving the street or the vehicle. This can save a great deal of time and money for saved man hours. This same technique of using an embodiment of the present invention may be used for inspecting components located adjacent to or on any building, not just residential houses.

In a fourth method of performing an inspection with an embodiment of the present invention, the inspection may be performed in stages. A first stage may be that the inspector views the area of inspection using the infrared camera system from a distance to make sure there is not a huge leak that the inspector is about to walk or drive into. This would be mainly for the safety of the inspector. Many chemicals have little or no odor and are invisible to the human eye. Hence, an inspector could be driving or walking right into a very dangerous situation. Next, after the inspector confirms that there is not a huge leak (e.g., large flow of chemical emanating from the site), the inspector can perform a more detailed inspection looking for medium, small, and/or very small leaks.

Sometimes gas or chemical leaks or chemical spills in cities or near highways are reported to the police first, and the police send out officers to direct traffic away from the gas/chemical leak for the safety of the public. However, there have been instances where an officer drives right into the stream of the leak without knowing it and ignites an explosion, which may injure or kill the officer. The same dangers exist for repair persons entering such a location. Thus, it would be beneficial to incorporate a method of using an embodiment of the present invention into a first response system. For example, if a chemical leak/spill is suspected, a helicopter with an infrared camera system of an embodiment may be flown toward the suspected location to assess it visually from a safe distance using a method of the present invention. By doing so, the magnitude and direction of the fumes from a leak or spill may be determined and reported quickly and safely. It is often difficult to initially determine the magnitude of the leak or spill using conventional methods. As another example, an embodiment of the present invention could be used by firemen from their fire truck as they approach a scene of a reported leak or spill. Likewise, a maintenance or safety crew at a processing plant equipped with an embodiment of the present invention could assess a situation from a safe distance as they enter to investigate a suspected leak or spill.

The aiming of the infrared camera system of an embodiment towards a component being inspected may be performed from a vehicle. Part or all of the system may be attached to the vehicle or supported by the vehicle, and/or may be held be a person in the vehicle, for example. It may be any type or kind of vehicle suitable for the inspection, including (but not limited to): a truck, a car, a motorcycle, a bicycle, a boat, a ship, a personal watercraft, a fixed-wing airplane, a rotary wing vehicle (e.g., helicopter, gyro-plane), a powered paraglider, an ultralight aircraft, a powered glider, a glider, a balloon, a blimp, a remote controlled vehicle, an unmanned aerial vehicle, and combinations thereof. The vehicle may be moving or stopped during part or all of the inspection. If the infrared camera system is mounted on or attached to a vehicle, it may be desirable to have the camera system mounted on some type of stabilizing platform or stand, as is commonly used in the movie filming industry (e.g., gyro-stabilized apparatus). Such a stabilizing platform may provide the ability to obtain better images of a test site from a moving vehicle (e.g., truck, ATV, helicopter, blimp, airplane).

An embodiment may be attached to a satellite to provide inspections from space. One of the advantages of infrared is that it can see through most clouds. The range of inspection is limited only by a line of sight for a method of inspecting using an embodiment of the present invention. Hence, as long as the chemical leak or the trail of fumes emitted from the leak are within a line of sight (e.g., not blocked by trees, heavy rain, buildings, or structures), an infrared image may be obtained. The size/type/configuration of lens can thus be increased/decreased/varied as needed to provide focus for a given range.

The typical method of finding leaks on cross country transmission lines is to walk along the lines using a sniffer device (flame-pack detector), or in some cases where there are no fences one may drive a truck or ATV with mounted sniffers, up and down the lines. One of the disadvantages of this method is that if the wind is blowing away from the sniffer or if the vehicle or the walker is upwind from the leak, the sniffer probably will not detect a leak; thus missing the leak altogether. The next problem is that a lot of the gathering lines have now been overgrown with houses, buildings, and backyard fences. This makes it very impractical to check for leaks in and around residential back yards using conventional techniques. Companies often perform aerial surveys to look for encroachments or blocking of their easement. Such surveys may be performed simultaneous with a visual infrared inspection for leaks.

Also, truck mounted sniffers are actually built for leak detection in the cities not for cross country transmission lines. The difference being that the size of leak in cities versus transmission lines can be great. There is a danger of a pickup with a hot catalytic converter with grass stuck to it being driven onto a 200 mcf per day leak. Such a scenario can result in an explosion that can kill the driver and destroy the equipment. The conventional leak survey equipment requires the inspector to be in close proximity within the stream of gas flow to detect it. By the time the gas is detected for a large leak, it may be too late. Using an embodiment of the present invention, a large leak may be seen from more than ½ mile away, and other leaks may be seen from a distance.

An embodiment of the present invention may be attached to a helicopter or plane, for example, and flown over a transmission line at a relatively high rate of speed (e.g., 60-120 mph) while visual images are recorded using the infrared camera system. Even though the speed may be too great for an inspector to spot a leak on-the-fly, a computer image recognition system may be able to detect the leak at the higher speed, or a second review playing back the recording at a slower speed may be able to catch missed leaks.

Often the leaks in transmission lines are found by locating dead vegetation where the gas is leaking through the ground. However, during the winter when the grass is brown, this method may not work. Also in some areas, such as desert areas, there may be no vegetation where the leak exists. Thus, using a method of the present invention, leaks from a buried transmission line may be easily detected visually from a short or long distance away with an embodiment of the present invention.

Down in the swamp land of southern Louisiana, for example, it is almost impossible to walk the lines. Instead, the operators typically fly over their lines and look for discolored vegetation. However, a colony of ants can also leave an area of discolored vegetation that looks like a gas leak from the air. With an embodiment of the present invention mounted on a helicopter, for example, one may hover over an area suspected of having a leak, and record a short sequence of the specific area using the infrared camera system 22 to easily determine if there is a leak. In alternative, the entire line may be visually scanned using an infrared camera system 22 to look for leaks.

Most transmission lines have pressure gauges and automated valves at certain intervals (check points) along the line. Often an operator has the equipment to see a pressure drop across the line between points which may be 50-100 miles apart, for example. Along such a long distance between the two points, there may be several leaks. Typically, it is difficult to determine which of the leaks is larger. Thus, many smaller leaks may be fixed before finding the larger leak. Using an embodiment of the present invention, the larger leaks may be distinguished from the smaller leaks. Thus, the larger leaks may be located and repaired first, as they are usually the first priority.

Sometimes when one leak is being repaired, it can cause a new leak in the same pipe at another location due to movement of the pipe during the repair operation. In a method of the present invention, the nearby portions of the repaired line may be quickly and easily inspected visually using an embodiment of the present invention to determine whether another leak exists along that line.

When cast iron or old metal lines develop leaks, the pipe material often becomes saturated with the leaking gas. Also, the dirt around and above a gas leak (for any type of pipe) often becomes saturated with gas. Thus, after performing a repair and replacing the dirt, a sniffer detector may falsely indicate that the leak is still present because it may be detecting the remaining gas saturated in the dirt and/or pipe. Also, if the gas is odorized, the smell will often linger for several days as it slowly dissipates from the dirt, which can lead to follow-up complaints by persons still smelling the gas. However, performing a visual gas leak inspection with an embodiment of the present invention, may quickly determine whether the leak still exists after the repairs (before or after replacing the dirt). In most cases, the visual test will be able to distinguish remaining petroleum products saturated in the dirt and an actual leak (showing a stream of blowing gas, for example). This can save companies a lot of money on service calls and ensure that the leaks are actually fixed more accurately and more reliably.

Leak surveys in downtown business districts often have to be conducted at night due to traffic. With proper flight clearance, an infrared camera system 22 may be mounted on a helicopter, for example, to perform these leak surveys from a helicopter during the daytime and save overtime hours for crews. One of the advantages of performing a leak survey from above using an infrared camera system 22 to visually detect leaks is that the ground often retains heat to provide a good thermal contrast and thus a better background contrast for viewing the leak with infrared, as compared to the sky or a structure in many cases.

Another method of using an embodiment of the present invention is the detection of leaks in large tanker vessels transporting petroleum products by sea. Using an infrared camera system of an embodiment of the present invention, leaks to the environment may be detected visually from a safe distance (e.g., on land, on a dock) by the shipping company or by enforcement/regulatory agencies (e.g., EPA, DOT). Such ships carrying chemicals or petroleum products may be visually inspected as they pass by or as they approach, for example.

Inspections may also be performed onboard the boat, ship, or vessel. Also, enclosed areas within a ship may be periodically or continuously monitored using a portable or permanently-installed/stationary infrared camera system of an embodiment, for example.

Another method of using an embodiment of the present invention is detecting gas leaks on petroleum production rigs. Often such rigs are approached via helicopter. An infrared camera system 22 adapted to visually image a petroleum product leak may be mounted on a crew helicopter. This would enable the crew on the helicopter to scan for gas leaks on gas platforms out in the ocean as they approach and before they land, for example. This would reduce or eliminate the risk of landing a helicopter with a hot engine into a gas leak. Furthermore, in another embodiment, a permanently-mounted/stationary infrared camera system 22 may be mounted at certain locations around the rig to provide a continuous or periodic visual leak survey.

In another method of using an embodiment of the present invention, detection of chemical leaks may be performed at factories, processing plants, manufacturing facilities, refineries, and/or petroleum separation plants. At some plants, they typically do monthly valve maintenance and inspections, for example. The problem with the way that they are currently done is that the flame-pack detector will often trigger on grease or WD-40 that is used on the valves for lubrication, for example. However, an infrared camera system 22 may be tuned (e.g., using an optical bandpass filter 46 having a certain pass band 80) so that it does not have the ability to see or detect these greases and lubricants. Hence, such an embodiment may distinguish between the lubricants and gas leaks. If the fumes of the greases and/or lubricants are imaged by the camera system 22, the visual observation of the fumes and the pattern of the fumes may allow the inspector to discern that it is not a leak and it is merely a lubricant evaporating. Often valves have been repacked due to a false leak detection triggered by lubricants on the valves, which is very costly and a waste of resources.

Another method of the present invention is the detection of leaks in the petrochemical industry or other chemical producing industries, using an embodiment of the present invention to visually detect leaks. Detection of such leaks may be performed at any stage from the exploration to the processing and production to the transporting of the chemicals produced to the containers storing the chemicals to the equipment using the chemicals, for example. A pipe or transportation line carrying the chemical may be visually inspected for leaks using an embodiment of the present invention. As another example, various pipes, connections, and equipment at a processing plant may be visually inspected or monitored for leaks using an embodiment of the present invention. Storage containers, cargo vessels, or truck trailers used for storing and/or transporting the chemicals may be visually inspected for leaks using an embodiment of the present invention, for example. Some example chemicals include (but are not limited to): ethylene, propylene, acetylene, propane, alcohol, ethanol, methanol, xylene, benzene, butadiene, acetone, compounds thereof, and combinations thereof.

An embodiment of the present invention may be used to perform a leak survey in and/or around a plant. An advantage of the present invention is that large leaks can be distinguished from small leaks, visually. Often the small leaks go unrepaired because they cannot be found easily using conventional methods. Even small leaks can be very dangerous in an enclosed area where flammable gases become trapped therein. Also, in many processing plants, the gases may have no odor added to them, which means a person would not smell the gases. Even where the gases are odorized, it is often difficult or impractical to detect all of the leaks. In most processing plants, the plant smells like chemicals everywhere because there are lots of small leaks. If the plant personnel could quickly and easily find the leaks, as they can using an embodiment of the present invention, it may become economical to fix even the smallest leaks. If that becomes the case, then processing plants may cease to smell like chemicals all the time. On one test of an embodiment of the present invention, 15 leaks were found in one region of a large plant in just 30 minutes, which is faster than most conventional methods of inspection. Another advantage of using an embodiment of the present invention is that the inspector often does not have to crawl on and around the equipment and pipes to find the leaks, as they may be seen with the infrared camera system when a line of sight is provided. Using a sniffer detector, however, an inspector would be required to get his detector within the flow of the gas leak to detect it.

Enclosed areas within a plant or any area at a plant may be periodically or continuously monitored using a portable or permanently-installed/stationary infrared camera system of an embodiment, for example. A permanently-mounted infrared camera of an embodiment may use a closed-cycle Stirling cryocooler, for example, and may be similar to the first embodiment of FIG. 1 but adapted to be mounted in a building. An entire network of permanently mounted cameras may be strategically located throughout a plant to provide partial or complete coverage of the plant. In one embodiment, a person may monitor the images provided by the cameras continuously or periodically. In another embodiment, a computer system with image recognition software may be used to detect changes in the image or motion in an image indicating a stream of gas or liquid flow at a leak.

Also, many plants or factories have blow-off valves that vent out of the roof. A single plant may have numerous vents with vent exits being more than 30 feet high. However, using an infrared camera system in accordance with the present invention, gases exiting such vents may be quickly surveyed from a distance on the ground, for example. Also, flare emissions burning on the top of a tower structure may be visually inspected using an embodiment of the present invention from a distance (e.g., more than 10 feet away, from the ground, etc.).

Recorded inspection data from prior inspections may be useful for a plant manager. If an inspection is performed in a plant and the same leak is found again in a subsequent survey, as documented visually with video by inspectors, the plant manager can then know that either the leak was never repaired or it is a re-occurring leak.

In yet another method of using an embodiment of the present invention, government regulatory agencies (e.g., railroad commission, DOT, EPA) may themselves perform visual inspections easily and quickly using an infrared camera system to determine if a plant or factory is emitting petroleum products or other chemicals that should not be emitted into the environment (e.g., volatile organic compounds, volatile inorganic compounds, nitrous oxide, unburned chemicals, etc.). Such inspections by government regulatory agencies may be performed randomly as surprise inspections to enforce stricter compliance with environmental rules and regulations. Also, government regulatory agencies may require recordings of inspections to be retained so that they can review them. Furthermore, a government regulatory agency may then perform follow-up inspections visually at targeted areas where a leak was known from a prior inspection to ensure that the leaks were repaired in a timely manner. A government regulatory agency may also review a series of test videos to look for unrepaired leak scenarios. Thus, there are numerous methods of using an embodiment of the present invention that may be useful to a government regulatory agency.

In another method of the present invention, fuel leaks (or other chemical or fluid leaks) on a vehicle may be easily found using an embodiment of the present invention. For example, on a Lotus Esprit car, the gas tanks are notorious for rusting and developing small pinhole leaks which are difficult to locate and find. It is not cost efficient to remove the gas tanks for inspection, as the engine must be removed to get the gas tanks out of the vehicle. Also, such cars are notorious for having leaks at high pressure and/or low pressure fuel lines, which can cause engine fires. Furthermore, the toxic fumes from an engine bay where a fuel leak exists often make there way into the cabin, which is dangerous and obnoxious for the cabin occupants. An embodiment of the present invention may be used to accurately pinpoint and find such leaks. Also, such a method may be applied to locate fuel leaks in other vehicles, such as airplanes, boats, helicopter, and personal watercraft, for example. An infrared camera system 22 of the present invention may be used to locate refrigerant leaks quickly on a vehicle. Also, an embodiment of the present invention may be used to locate gas or refrigerant leaks in home or building HVAC equipment.

FIGS. 23A-31B are some images generated by an embodiment of the present invention during experimental testing. Specifically, FIGS. 23A-31B were generated using the fourteenth embodiment (see FIG. 20) having an optical bandpass filter 46 with a pass band 80 about the same as that shown in FIG. 4.

FIGS. 23A-23D are visible images representing filtered infrared images of a gas 140 leaking from the ground (e.g., a buried line). The images of FIGS. 23A-23D are from a sequence of images extracted from a video recording of this leak 140. Although sometimes difficult to illustrate in still images, the movement of the leak stream 140 in a video (sequence of images) makes the leak 140 much more apparent. Very small leaks (low flowrate) that do not show up in one still image are often easily seen in a video because the movement of the leak stream or fumes can be seen in a video.

FIGS. 24A-24D are images obtained by an embodiment of the present invention showing a gas 140 leaking from a compressor at a flange 142 on the discharge side. The sequence of images in FIGS. 24A-24D were extracted from a video showing the gas 140 streaming from the flange 142.

FIGS. 25A-25D are images obtained by an embodiment of the present invention showing a natural gas (methane) leak 140 resulting from a crew cutting 1½ inch gas line with approximately 12 psi pressure. It is an underground gas line (not shown). Although the large cloud of methane 140 exiting the hole in the ground is somewhat dispersed and difficult to see in the still images of FIGS. 25A-25D, it is easily seen in the video due to the movement of the cloud 140. Note also that the images of background objects are easy to discern and focused in the original video, which aids in providing a context of where the leak 140 is coming from.

Figure 26:
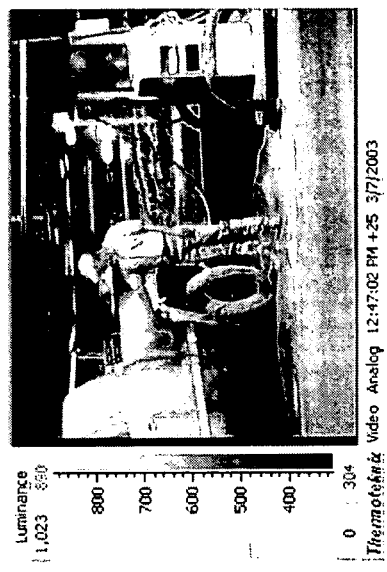

FIG. 26 is an image obtained by an embodiment of the present invention and extracted from a recorded video sequence. FIG. 26 shows a large gas leak 140 emanating from a component 144 in a processing plant.

Figure 27:
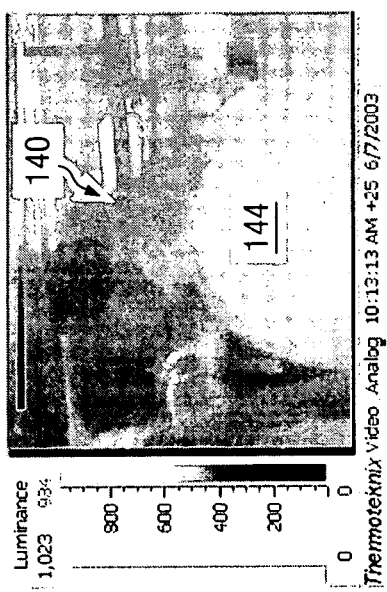

FIG. 27 is also an image obtained by an embodiment of the present invention and extracted from a recorded video sequence. FIG. 27 shows a gas 140 flowing from a vent tube 146 extending from a building roof 148 (about 30 feet high). This image was obtained by a person at ground level. The gas flowing out of the vent 146 may be from a blow-off valve that is exhausting to the environment, which may be indicative of a condition at that component causing the blow-valve to be opened.

Figure 28A:
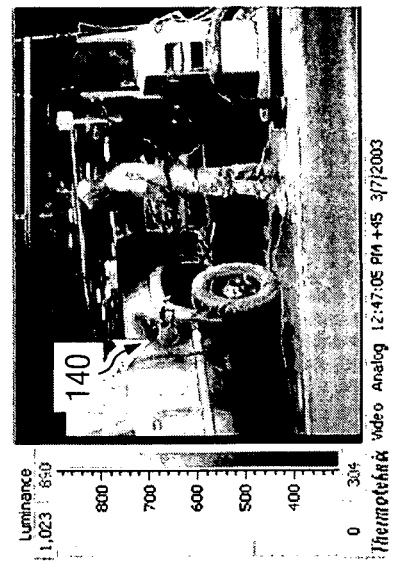
Figure 28B:
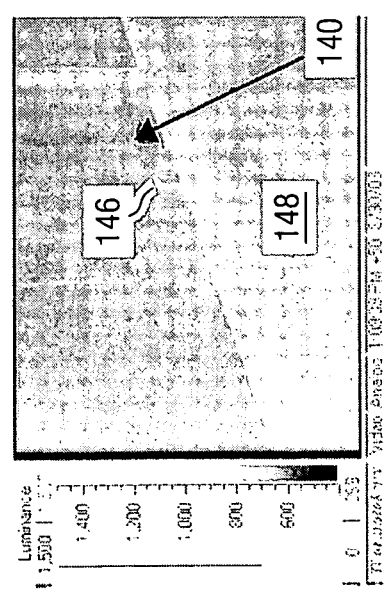

FIGS. 28A and 28B are more images obtained by an embodiment of the present invention and extracted from a recorded video sequence. FIGS. 28A and 28B show a man pumping gasoline into his truck at a gas pump. Note in FIG. 28B that as the gas is pumping into the gas tank, the gas fumes 140 can be seen just above the pump handle with the truck bed as the background.

Figure 29:
Figure 30:

FIG. 29 shows an image of propane 140 exiting a propane bottle in a test of the system for detecting propane. FIG. 30 shows an image of a small gas leak 140 emanating from a component at a processing plant. The leak appears as a faint black cloud 140 in the image. This is a relative small leak.

Figure 31A:
Figure 31B:
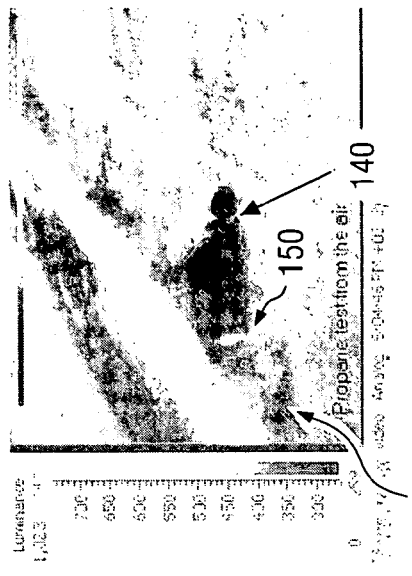

FIGS. 31A and 31B are images taken from a helicopter flying over a test site. In this test, a propane bottle was opened, as in FIG. 29, in a field. In FIG. 31A, the propane stream 140 can be seen with the infrared camera system at ½ mile away while the helicopter is moving toward the test site at about 60 knots. FIG. 31B is a more focused image of the propane stream 140 at a closer distance than that of FIG. 31A. Note that a person 150 can be seen standing next to the propane stream 140 and next to a bush 152 in FIG. 31B. Also, note that two roads can be seen in FIGS. 31A and 31B, which provide reference points and context of the location of the propane stream 140.

An advantage of an embodiment of the present invention, as illustrated in these images of FIGS. 23A-31B, is that often the background and surrounding objects can be clearly seen in the image along with the leak or stream of gas 140. This can be very useful in providing a reference or context of where the leak is located and aids in documenting the leak using video images.

In a recent test of an embodiment of the present invention before the US EPA, in comparison with other infrared camera systems, the embodiment of the present invention greatly outperformed the other systems. After this test before the US EPA, new US EPA regulations are expected to be released by the end of 2004, or shortly thereafter, allowing for the use of infrared camera systems to perform visual leak surveys. This demonstrates a long felt need in the industry that others have failed to meet, and that an embodiment of the present invention is now able to fulfill.

Also, after the US EPA test described above, there has been an explosive demand for embodiments of the present invention and for services using an embodiment of the present invention. This demonstrates the commercial success and great demand for embodiments of the present invention and for services using embodiments of the present invention.

Figure 32:
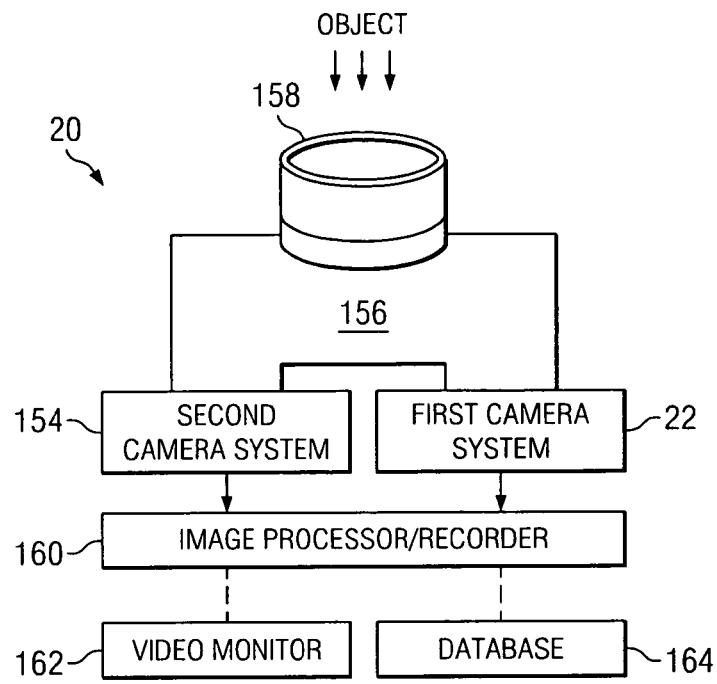
FIG. 32 is a schematic of a dual camera embodiment of the present invention.

FIG. 32 illustrates a schematic of a first dual camera embodiment of the present invention. This system includes a first video camera 22, which is an infrared camera system with an optical bandpass filter 46 (preferably installed in a refrigerated portion 42 thereof, i.e., cold filter configuration); a second video camera 154 (e.g., another infrared camera system); an image splitter 156; a lens assembly 158; and an image processor/recorder 160. The second video camera 154 may be any infrared camera system that can obtain an image from the same type of lens as the first video camera 22. The second video camera 154 may be an infrared camera with filters so that it will not image the leaking chemical. The first video camera 22 is an infrared camera adapted to provide a focused visual image of a chemical leak by using an optical bandpass filter 46 for a specific pass band 80 (e.g., pass band 80 with a wavelength range centered at about 3.38 microns). For example, the first video camera 22 may be any of the embodiments discussed above (see e.g., FIGS. 1-20). The first video camera 22 may receive the same image as the second video camera 154 from the same lens 158 via the image splitter 156. The video signal from each camera may be output to the image processor/recorder 160. The image processor/recorder 160 may simply record the two video feeds for later processing. In an alternative, the image processor/ recorder 160 may be a system (e.g., a computer system running software for processing the video data) or specialized/dedicated hardware for processing the two video feeds. Preferably, the images from the second video camera 154 are compared to the images from the first video camera 22 by a software program running on a computer system. Because a gas leak, for example, will not appear in the image from the second video camera 154, the presence of the gas plume shown in the infrared image from the first camera 22 may be detected as a difference in the two video feeds.

In one embodiment, the software may automatically identify and map the pixel locations in the images for these differences corresponding to the gas plume in the infrared image. Then, the image of the gas plume (the differences shown in the infrared images from the first camera) is highlighted or colored to make it stand out in the image.

Optionally, the image processor/recorder 160 may be communicably coupled to a video monitor 162 (see FIG. 32) and/or a database 164, for example. The video monitor 162 may be used for an operator or inspector to view any one or more of the images or all of the images obtained while using the system 20, for example. The database may be used as a repository or archive for the collected video images and test results. The first and second cameras 22, 154 may be separate devices. In another embodiment, the image splitter 156, lens 158, first camera 22, and second camera 154 may be integrally placed within a single portable unit. Likewise, the image processor/recorder 160 (or some portion thereof) may be placed within the same enclosure or on the same rack as the remainder of the system 20.

Figure 33:
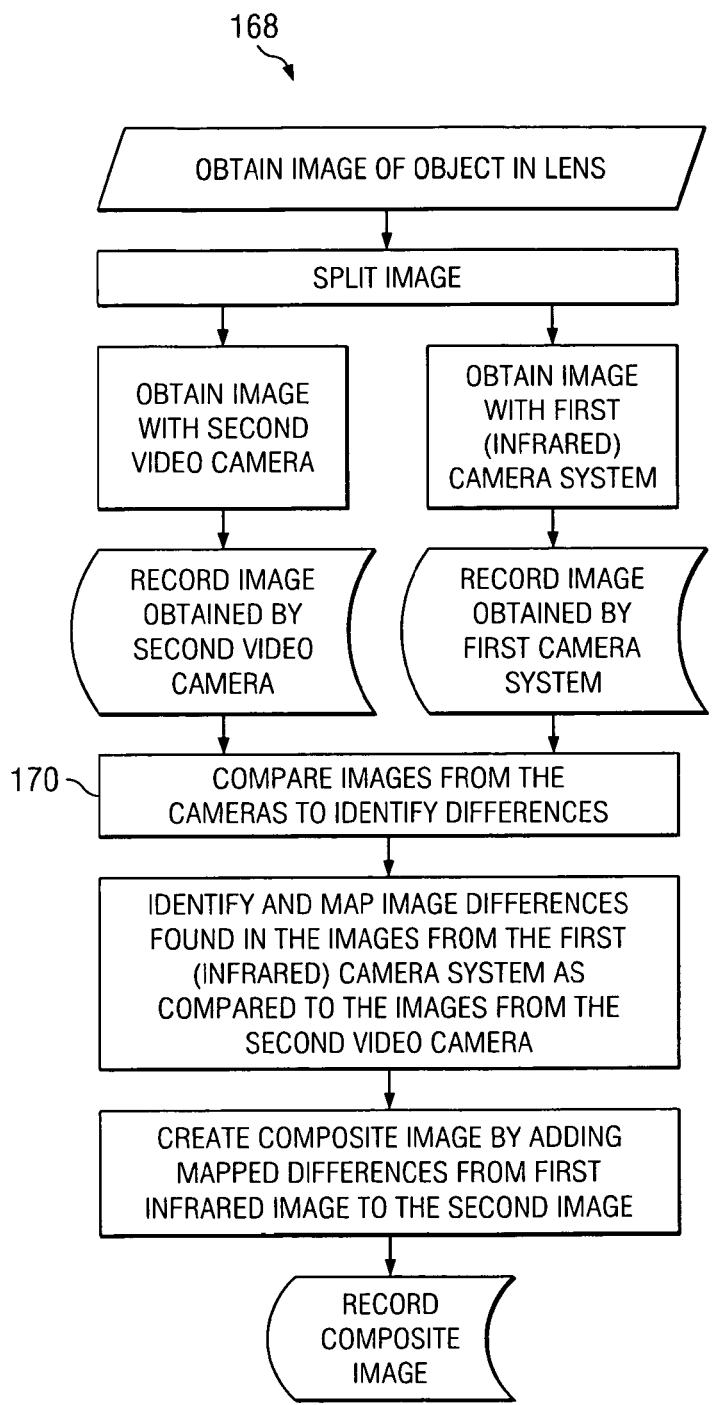
FIGS. 33-35 are flowcharts illustrating methods of using a dual camera embodiment of the present invention.

FIG. 33 is a flowchart 168 showing an illustrative method that may be used for an embodiment (e.g., the embodiment shown in FIG. 32) of the present invention. In this method of FIG. 33, the images from both cameras may be recorded in the field and later processed in a vehicle or office. Also, using the method of FIG. 33, the images of both cameras may be stored before being processed, even though the processing may be performed immediately thereafter (on-the-fly). The images from both cameras are compared to identify the differences (see block 170), which may be indicative of chemical leak. Next, the differences are identified and mapped out. The mapped differences may then be added to the image from the second camera to provide a composite image. Also, when differences are identified (e.g., exceeding a predetermined number of pixels within the image, detecting movement), an alarm may be triggered to notify an operator or inspector of the suspected detection of a chemical leak.

Figure 34:
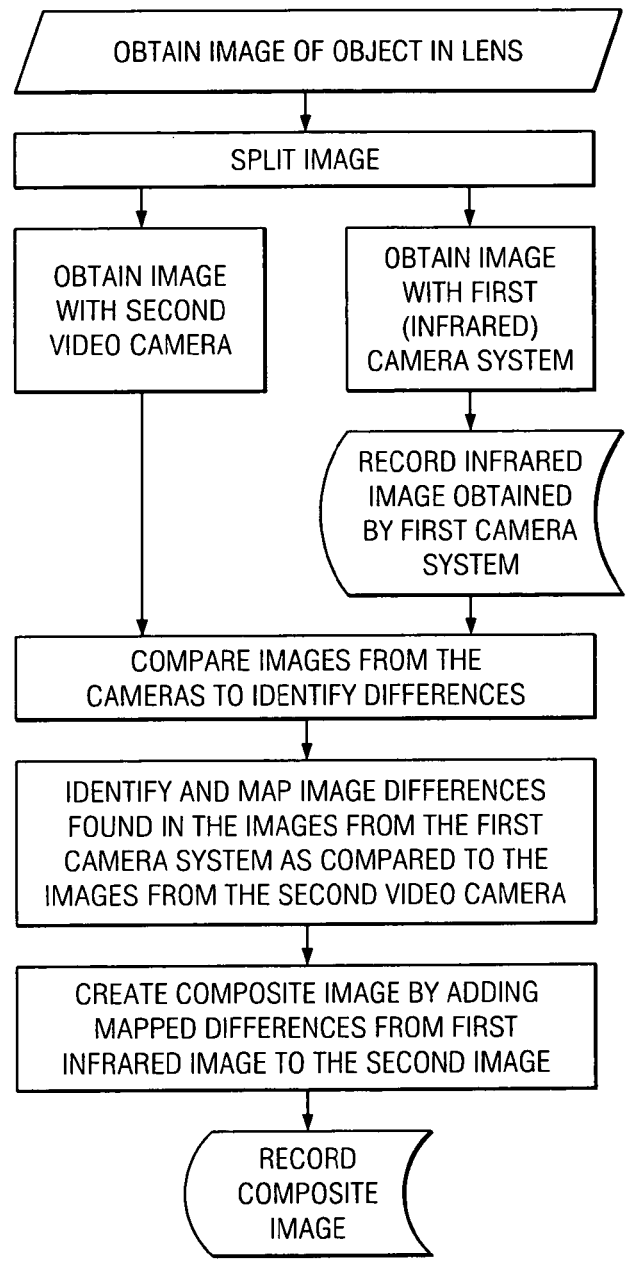

In another method, illustrated in FIG. 34, the infrared image from the first camera 22 and the composite image may be recorded. For example, the infrared image from the first camera may be needed for record keeping to maintain an unmodified image. However, the composite image may be preferred for reviewing by the inspections or for studying the inspections, as it may provide color coding or other visual or audio cues to help the reviewer to better identify potential leaks.

Figure 35:
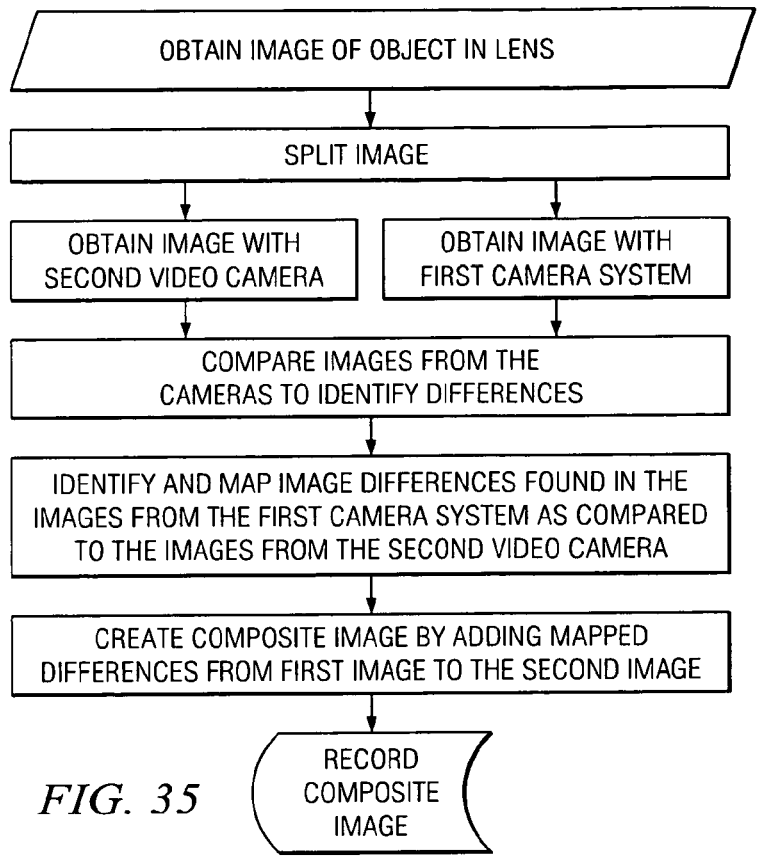

In still another method, illustrated in FIG. 35, only the composite image may be recorded and the processing of the images may be performed as the images are collected. However, a temporary buffer memory (e.g., DRAM, MRAM) may be used during the processing.

Figure 37:
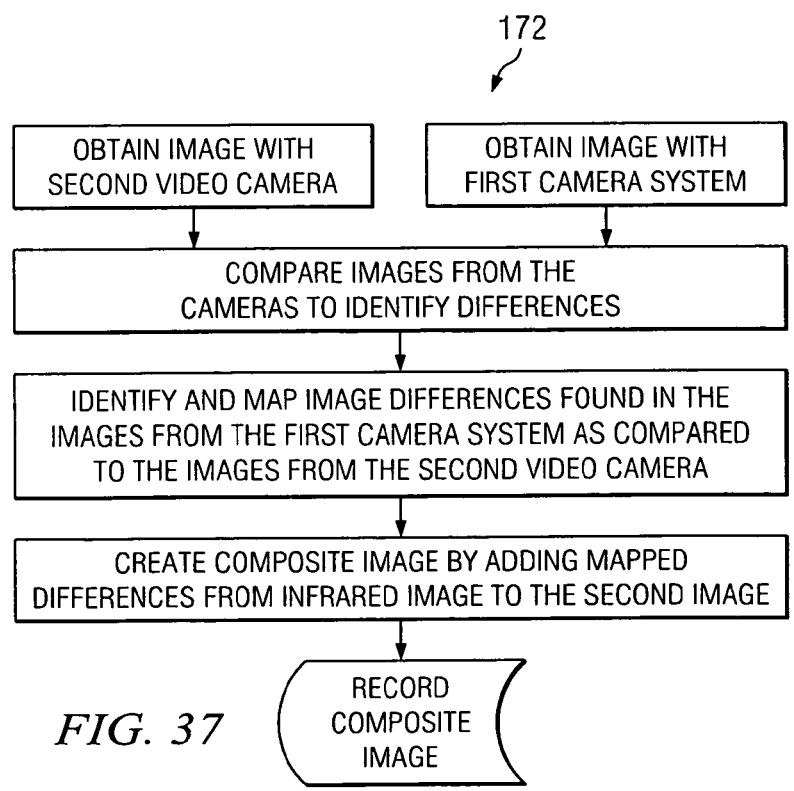
FIGS. 37 and 38 are flowcharts illustrating more methods of using a dual camera embodiment of the present invention.
Figure 36:
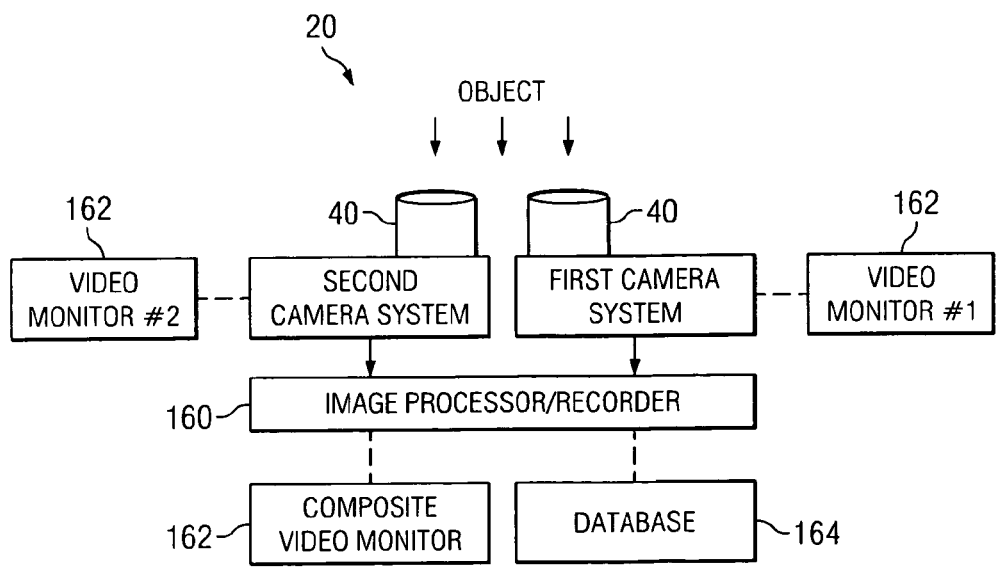
FIG. 36 is a schematic of another dual camera embodiment of the present invention.

FIG. 36 shows a simplified schematic for an alternative system 20 where the image splitter and mutual lens are not used. Thus, the first camera 22 receives its images separately from the second camera 154. In this configuration, the second camera 154 may be a visible light camera, for example. FIG. 37 shows an illustrative flowchart 172 for a method where the system 20 of FIG. 36 may be used. The method of the FIG. 37 flowchart may be varied to provide a recording of the image(s) from the first and/or second cameras 22, 154. In other embodiments, additional camera(s) (not shown) may be used as well (e.g., third camera). A video image from the second video camera 154 may be shown within a video image from the first camera 22 (picture-in-picture) to provide a reference view (e.g., full color visible light image) for the infrared image from the first camera 22.

Figure 38:
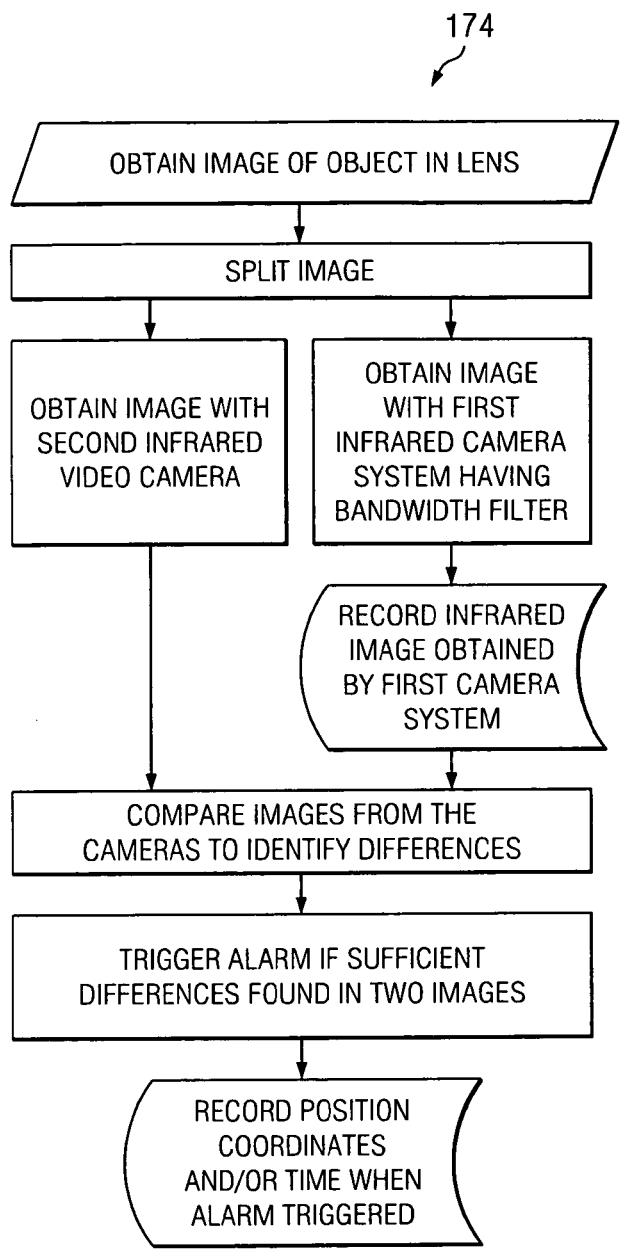

FIG. 38 shows an illustrative flowchart 174 for a method of an embodiment of the present invention. In this method, an alarm may be triggered if the comparison of images from the first and second cameras shows sufficient differences above a predetermined threshold (e.g., area of pixels, number of pixels, number of pixels per area, etc.) or movement in the image from the first camera that is not in the image from the second camera.

In another embodiment, one stationary-mounted camera (e.g., in an engine room) may be used. Often in certain areas of a plant there is rarely movement (e.g., no people moving about the room most times) in the room (other than unseen internal parts). In such embodiment, the image may be monitored by hardware or a computer system to detect movement in the image. Because the image is an infrared image taken with an infrared camera system of an embodiment, the movement may be caused by a chemical leak. Thus, the image may be continuously or periodically monitored for movement automatically. An alarm may be triggered when movement is detected to alert an operator to the suspected leak. Then, the operator may view the video image (past or present) to see if there is an actual leak.

In accordance with another aspect of the present invention, a passive infrared camera system adapted to provide a visual image of a chemical emanating from a component having the chemical therein, is provided. The passive infrared camera system includes a lens, a refrigerated portion, and a refrigeration system. The refrigerated portion includes therein an infrared sensor device adapted to capture an infrared image from the lens, and an optical bandpass filter located along an optical path between the lens and the infrared sensor device, wherein at least part of a pass band for the optical bandpass filter is within an absorption band for the chemical. The refrigeration system is adapted to cool the refrigerated portion of the infrared camera system.

The refrigeration system may include a chamber adapted to retain liquid nitrogen, for example. As another example, the refrigeration system may include a closed-cycle Stirling cryocooler. The refrigeration system may include a cryocooler system adapted to cool the infrared sensor device and the optical bandpass filter to a temperature below about 100 K. The passive infrared camera system is preferably portable and further includes a battery adapted to provide power for the infrared camera system during use of the infrared camera system. The passive infrared camera system may include a frame, a shoulder-rest portion extending from the frame, and a handle extending from the frame. The passive infrared camera system preferably includes a flat-panel screen adapted to display images obtained by the infrared camera system during use of the infrared camera system. The passive infrared camera system may further include a light shield located proximate to the screen and adapted to at least partially shield the screen from ambient light.

The optical bandpass filter may be adapted to allow a transmittance greater than about 45% of infrared light between about 3360 nm and about 3400 nm to pass therethrough, for example. As another example, the optical bandpass filter may be adapted to allow a transmittance greater than about 45% of infrared light between about 3350 nm and about 3390 nm to pass therethrough. The pass band of the optical bandpass filter may have a center wavelength located between about 3360 nm and about 3400 nm, for example. As another example, the pass band of the optical bandpass filter may have a center wavelength located between about 3375 nm and about 3385 nm, wherein the bandpass filter is adapted to allow a transmittance greater than about 80% of infrared light between about 3365 nm and about 3395 nm to pass therethrough, wherein the bandpass filter comprises a silicon dioxide substrate, and wherein the pass band has a full width at half maximum transmittance that is less than about 80 nm. As yet another example, the pass band of the optical bandpass filter may have a center wavelength located between about 3340 nm and about 3440 nm, wherein the bandpass filter is adapted to allow a transmittance greater than about 70% at the center wavelength, and wherein the pass band has a full width at half maximum transmittance that is less than about 100 nm. As still another example, the pass band of the optical bandpass filter may have a center wavelength between about 3360 nm and about 3380 nm, wherein the bandpass filter is adapted to allow a transmittance greater than about 70% at the center wavelength, and wherein the pass band has a full width at half maximum transmittance that is less than about 100 nm.

The infrared sensor device may include an Indium Antimonide focal plane array, wherein the focal plane array is enclosed in an evacuated Dewar assembly. The pass band may have a full width at half maximum transmittance that is less than about 600 nm, for example. As another example, the pass band may have a full width at half maximum transmittance that is less than about 400 nm. As yet another example, the pass band may have a full width at half maximum transmittance that is less than about 200 nm. As still another example, the pass band may have a full width at half maximum transmittance that is less than about 100 nm. The pass band for the optical bandpass filter may be located between about 3100 nm and about 3600 nm, for example. As another example, the pass band for the optical bandpass filter may be located between about 3200 nm and about 3500 nm. As yet another example, the pass band for the optical bandpass filter may be located between about 3300 nm and about 3500 nm. The pass band for the optical bandpass filter may have a center wavelength located within the absorbance band for the chemical.

The component being inspected may be a pipe, a compressor, an engine, a valve, a container, a tank, a switch, a reservoir, a fitting, a connector, a hose, a flare, an exhaust outlet, a machine, a vent for a blow-off valve, or combinations thereof, for example. The refrigerated portion may be defined by an interior of a Dewar container. The chemical may be methane, ethane, propane, butane, hexane, ethylene, propylene, acetylene, alcohol, ethanol, methanol, xylene, benzene, butadiene, formaldehyde, acetone, gasoline, diesel fuel, or combinations thereof, for example. The chemical may be petroleum, petroleum by-product, volatile organic compound, volatile inorganic compound, or combinations thereof, for example. The chemical may include a hydrocarbon, for example. As another example, the chemical may include methane, wherein the absorption band is at least partially located between about 3100 nm and about 3600 nm, wherein the pass band is located between about 3100 nm and about 3600 nm. The chemical may include methane, wherein the absorption band is at least partially located between about 7200 nm and about 8200 nm, wherein the pass band is located between about 7200 nm and about 8200 nm, for example. As yet another example, the chemical may include sulfur hexafluorine, wherein the absorption band is at least partially located between about 10400 nm and about 10700 nm, wherein the pass band is located between about 10400 nm and about 10700 nm. As still another example, the chemical may include ethylene, wherein the absorption band is at least partially located between about 3100 nm and about 3500 nm, wherein the pass band is located between about 3100 nm and about 3500 nm. The chemical may include ethylene, for example, wherein the absorption band is at least partially located between about 10400 nm and about 10700 nm, wherein the pass band is located between about 10400 nm and about 10700 nm. As another example, the chemical may include propylene, wherein the absorption band is at least partially located between about 3100 nm and about 3600 nm, wherein the pass band is located between about 3100 nm and about 3600 nm. As yet another example, the chemical may include propylene, wherein the absorption band is at least partially located between about 10000 nm and about 11500 nm, wherein the pass band is located between about 10000 nm and about 11500 nm. As still another example, the chemical may include 1,3 butadiene, wherein the absorption band is at least partially located between about 3100 nm and about 3200 nm, wherein the pass band is located between about 2900 nm and about 3200 nm. As a further example, the chemical may include 1,3 butadiene, wherein the absorption band is at least partially located between about 9000 nm and about 12000 nm, wherein the pass band is located between about 9000 nm and about 12000 nm.

The passive infrared camera system may include a video recording device adapted to record images obtained by the infrared camera system during use of the infrared camera system. The infrared camera system may be non-radiometric. The infrared camera system is preferably portable and non-radiometric.

In accordance with yet another aspect of the present invention, a passive infrared camera system adapted to provide a visual image of a chemical emanating from a component having the chemical therein, is provided. The passive infrared camera system includes a lens, a refrigerated portion, and a refrigeration system. In this case, the refrigerated portion includes therein an infrared sensor device adapted to capture an infrared image from the lens, and an optical bandpass filter located along an optical path between the lens and the infrared sensor device, the optical bandpass filter having a pass band with a full width at half maximum transmittance being less than about 600 nm, wherein at least part of the pass band for the optical bandpass filter is within an absorption band for the chemical. The refrigeration system is adapted to cool the refrigerated portion of the infrared camera system.

In accordance with still another aspect of the present invention, a passive infrared camera system adapted to provide a visual image of a chemical emanating from a component having the chemical therein, is provided. The passive infrared camera system includes a lens, a refrigerated portion, and a refrigeration system. In this case, the refrigerated portion includes therein an infrared sensor device adapted to capture an infrared image from the lens, and an optical bandpass filter located along an optical path between the lens and the infrared sensor device, wherein a pass band for the optical bandpass filter is located between about 3100 nm and about 3600 nm. The refrigeration system is adapted to cool the refrigerated portion of the infrared camera system.

In accordance with a further aspect of the present invention, a passive infrared camera system adapted to provide a visual image of a chemical emanating from a component having the chemical therein, is provided. The passive infrared camera system includes a lens, a refrigerated portion, a refrigeration system, and a battery. The refrigerated portion includes therein an infrared sensor device adapted to capture an infrared image from the lens, and an optical bandpass filter located along an optical path between the lens and the infrared sensor device, wherein at least part of a pass band for the optical bandpass filter is within an absorption band for the chemical. The refrigeration system is adapted to cool the refrigerated portion of the infrared camera system. The battery is electrically coupled to the infrared camera system, the infrared camera being adapted to be powered by the battery during use of the chemical leak inspection system.

In accordance with another aspect of the present invention, a portable chemical leak inspection system that includes a passive infrared camera system adapted to provide a focused visual image of a chemical emanating from a component having the chemical therein, is provided. The passive infrared camera system includes a lens, a refrigerated portion, and a refrigeration system. The refrigerated portion includes therein an infrared sensor device adapted to capture an infrared image from the lens, and an optical bandpass filter located along an optical path between the lens and the infrared sensor device, wherein at least part of a pass band for the optical bandpass filter is within an absorption band for the chemical. The refrigeration system is adapted to cool the refrigerated portion of the infrared camera system. The portable chemical leak inspection system also includes a battery, a frame, a shoulder-rest portion, and a handle. The battery is electrically coupled to the infrared camera system, the infrared camera being adapted to be powered by the battery during use of the chemical leak inspection system. The frame is attached to the infrared camera system. The shoulder-rest portion extends from the frame. And, the handle extends from the frame.

In accordance with yet another aspect of the present invention, a portable chemical leak inspection system that includes a passive infrared camera system adapted to provide a focused visual image of a chemical emanating from a component having the chemical therein, is provided. The passive infrared camera system includes a lens, a refrigerated portion, and a refrigeration system. In this case, the refrigerated portion includes therein an infrared sensor device adapted to capture an infrared image from the lens, and an optical bandpass filter located along an optical path between the lens and the infrared sensor device, wherein a pass band for the optical bandpass filter is located between about 3100 nm and about 3600 nm, and wherein the pass band has a full width at half maximum transmittance that is less than about 600 nm. The refrigeration system is adapted to cool the refrigerated portion of the infrared camera system. The portable chemical leak inspection system also includes a battery, a frame, a shoulder-rest portion, and a handle. The battery is electrically coupled to the infrared camera system, the infrared camera being adapted to be powered by the battery during use of the chemical leak inspection system. The frame is attached to the infrared camera system. The shoulder-rest portion extends from the frame. And, the handle extends from the frame.

In accordance with still another aspect of the present invention, a portable passive infrared camera system adapted to provide a focused visual image of a chemical emanating from a component having the chemical therein, is provided. The infrared camera system includes a lens, a Dewar container, and a refrigeration system. The Dewar container defines a refrigerated portion therein. The refrigerated portion includes therein an infrared sensor device having an array of sensors adapted to receive an infrared image from the lens and adapted to generate electrical signals corresponding to the infrared image, and an optical bandpass filter located along an optical path between the lens and the infrared sensor device, wherein a pass band for the optical bandpass filter is located between about 3100 nm and about 3600 nm, and wherein the pass band has a full width at half maximum transmittance that is less than about 600 nm. The refrigeration system is adapted to cool the refrigerated portion.

In accordance with a further aspect of the present invention, a portable passive infrared camera system adapted to provide a focused visual image of a chemical emanating from a component having the chemical therein, is provided. The infrared camera system includes a lens, a Dewar container, and a refrigeration system. The Dewar container defines a refrigerated portion therein. In this case, the refrigerated portion includes therein an infrared sensor device having an array of sensors adapted to receive an infrared image from the lens and adapted to generate electrical signals corresponding to the infrared image, and an optical bandpass filter located along an optical path between the lens and the infrared sensor device, wherein a pass band for the optical bandpass filter is located between about 3200 nm and about 3500 nm, wherein the pass band has a full width at half maximum transmittance that is less than about 80 nm, and wherein the pass band has a center wavelength located between about 3320 nm and about 3440 nm. The refrigeration system is adapted to cool the refrigerated portion.

Although embodiments of the present invention and at least some of its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system for producing a visible image of a leak of any one or more chemicals of a group of chemicals, the leak emanating from a component, including:
 a passive infrared camera system including:
 a lens assembly including a lens;
 a refrigerated portion including an interior;
 an infrared sensor device located in the interior of the refrigerated portion;
 a single filter configuration located in the interior of the refrigerated portion and including an optical bandpass filter fixed along an optical path between the lens assembly and the infrared sensor device;
 a refrigeration system that can cool the interior of the refrigerated portion;
 wherein at least part of the pass band for the single filter configuration is within an absorption band for each of the chemicals; and
 wherein the aggregate pass band for the single filter configuration is at least about 100 nm; and
 a processor that can process a signal representing the filtered infrared image captured by the infrared sensor device to produce a visible image of the chemical emanating from the component under variable ambient conditions of the area around the leak.

2. The system of claim 1, further including a recording device that can record the visible image of the leaking chemical.

3. The system of claim 2, wherein the recorded visible image can be viewed at a time other than when recorded.

4. The system of claim 2, wherein the recording device can record the visible image along with inspection information about the image selected from a group consisting of inspection location name, inspection location address, component name, component identification information, global positioning coordinates, a date, a time of day, an inspector's name, an inspection company's name, one or more camera system setting values, and combinations thereof.

5. The system claim 2, further including a voice recorder that can record voice notes along with the image.

6. The system of claim 1, wherein the passive infrared camera system further includes a display screen that can display the visible image of the leaking chemical.

7. The system of claim 1, wherein the passive infrared camera system is powered by a battery and is portable.

8. The system of claim 1, wherein the passive infrared camera system lens assembly includes more than one lens.

9. The system of claim 1, wherein the passive infrared camera system lens assembly is removable.

10. The system of claim 1, wherein the refrigerated portion is defined by a Dewar container.

11. The system of claim 1, wherein the refrigeration system includes a closed-cycle Stirling cryocooler.

12. The system of claim 1, wherein the refrigeration system can cool the interior of the refrigerated section to a temperature below about 100 K.

13. The system of claim 1, wherein the processor can process the filtered infrared image captured by the infrared sensor device to produce a visible image of more than one chemical.

14. The system of claim 1, wherein the infrared sensor device captures multiple images and the processor can process the multiple images to produce a visible video of the leak.

15. The system of claim 1, wherein, in use, the infrared sensor device receives a filtered infrared image from the single filter configuration and converts the filtered image to an electrical signal representing the filtered infrared image.

16. The system of claim 1, wherein the processor is part of the passive infrared camera system.

17. The system of claim 1, wherein the processor is separate from the passive infrared camera system.

18. The system of claim 1, wherein the image can be processed in real time.

19. The system of claim 1, further including a transmitter that can transmit the visible image to a location remote from the passive infrared camera system.

20. The system of claim 18, wherein the transmitter can transmit the image using at least one of a cable, a wire, a wireless communication device, a network connection, the Internet, or combinations thereof.

21. The system of claim 1, wherein the any one or more chemicals includes one or more substances selected from the group consisting of refrigerant; fuel; water vapor; methane; ethane; propane; butane; hexane; ethylene; propylene; o-xylene; toluene; benzene; acetylene; alcohol; ethanol; methanol; xylene; benzene; formaldehyde; 1,2 butadiene; 1,3 butadiene; butadiene; acetone; gasoline; diesel fuel; petroleum; petrochemicals; petroleum by-product; volatile organic compound; volatile inorganic compound; crude oil products; crude oil by-products; a hydrocarbon; and compounds and combinations thereof.

22. The system of claim 1, wherein the filter configuration includes more than one filter.

23. The system of claim 1, wherein the aggregate pass band for the single filter configuration is at least about 200 nm.

24. The system of claim 1, wherein the pass band for the filter configuration has a center wavelength located between about 3375 nm and about 3385 nm.

25. The system of claim 1, wherein the pass band for the filter configuration has a center wavelength located between about 3340 nm and about 3440 nm.

26. The system of claim 1, wherein the pass band for the filter configuration has a center wavelength located between about 3360 nm and about 3380 nm.

27. The system of claim 1, wherein the pass band for the filter configuration is located between about 2900 nm and about 3200 nm.

28. The system of claim 1, wherein the pass band for the filter configuration is located between about 3100 nm and about 3500 nm.

29. The system of claim 1, wherein the pass band for the filter configuration is located between about 3100 nm and about 3500 nm.

30. The system of claim 1, wherein the pass band for the filter configuration is located between about 3200 nm and about 3500 nm.

31. The system of claim 1, wherein the pass band for the filter configuration is located between about 3300 nm and about 3500 nm.

32. The system of claim 1, wherein the pass band for the filter configuration is located between about 3200 nm and about 3400 nm.

33. The system of claim 1, wherein the pass band for the filter configuration is located between about 9000 nm and about 12000 nm.

34. The system of claim 1, wherein the pass band for the filter configuration is located between about 10400 and 10700 nm.

35. The system of claim 1, wherein the pass band for the filter configuration is located between about 10000 nm and about 11500 nm.

36. The system of claim 1, wherein the pass band for the filter configuration is located between about 10500 nm and about 10600 nm.

37. The system of claim 1, wherein the pass band for the filter configuration has a full width at half maximum transmittance that is less than about 600 nm.

38. The system of claim 1, wherein the pass band for the filter configuration has a full width at half maximum transmittance that is less than about 400 nm.

39. The system of claim 1, wherein the pass band for the filter configuration is located between about 3250 nm and about 3510 nm with a full width at half maximum less than about 250 nm.

40. The system of claim 1, wherein the pass band for the filter configuration is located between about 3200 nm and about 3580 nm with a full width at half maximum less than about 350 nm.

41. The system of claim 1, wherein the pass band for the filter configuration is located between about 7600 nm and about 7800 nm.

42. The system of claim 1, wherein the pass band for the filter configuration is located between about 3200 nm and about 3500 nm with a full width at half maximum less than about 300 nm.

43. The system of claim 1, wherein the pass band for the filter configuration is located between about 3200 nm and about 3600 nm with a full width at half maximum less than about 400 nm.

44. The system of claim 1, wherein the filter configuration allows a transmittance greater than about 70% at the center wavelength of the pass band.

45. The system of claim 1, wherein the aggregate pass band for the filter configuration includes a full width at half maximum transmittance that is less than about 600 nm.

46. The system of claim 1, wherein the center wavelength of the pass band for the filter configuration is within an absorption band for one of the chemicals.

47. The system of claim 1, wherein the center wavelength of the pass band for the filter configuration is outside an absorption band for one of the chemicals.

48. The system of claim 1, wherein the absorption band of one of the chemicals includes a peak and the pass band for the filter configuration is centered at or close to the peak.

49. The system of claim 1, wherein the absorption band of one of the chemicals includes a peak and the pass band for the filter configuration is not centered at or close to the peak.

50. The system of claim 1, further including a computer programmed with image recognition software to analyze the image from the processor.

51. The system of claim 1, wherein the passive infrared camera system is attached to or supported by a movable vehicle selected from the group consisting of a motorcycle, a car, a truck, a bicycle, a boat, a ship, a personal watercraft, a rotary wing vehicle, an airplane, a powered paraglider, an ultralight aircraft, a powered glider, a glider, a balloon, a blimp, a remotely controlled vehicle, an unmanned aerial vehicle, a satellite, and combinations thereof.

52. The system of claim 1, wherein the passive infrared camera system is non-radiometric.

53. The system of claim 1, wherein the infrared sensor device includes an Indium Antimonide focal plane array of at least 81,920 sensor elements.

54. The system of claim 1, wherein the passive infrared camera system is attached to a permanently installed mount.

55. The system of claim 1, further including more than one passive infrared camera system.

56. The system of claim 55, wherein the passive infrared cameras are part of a network.

57. The system of claim 1, wherein the optical bandpass filter includes a silicon dioxide substrate.

58. The system of claim 1, wherein the refrigeration system includes a chamber adapted to retain liquid nitrogen.

* * * * *